United States Patent
Son et al.

(10) Patent No.: US 11,889,800 B2
(45) Date of Patent: Feb. 6, 2024

(54) METHOD AND SYSTEM FOR SETTING ARTIFICIAL ULTRAVIOLET ILLUMINATION FOR PLANT

(71) Applicants: SEOUL NATIONAL UNIVERSITY R&DB FOUNDATION, Seoul (KR); CHUNGBUK NATIONAL UNIVERSITY INDUSTRY-ACADEMIC COOPERATION FOUNDATION, Cheongju-si (KR)

(72) Inventors: Jung Eek Son, Seoul (KR); Hyo In Yoon, Seoul (KR); Myung Min Oh, Cheongju-si (KR)

(73) Assignees: SEOUL NATIONAL UNIVERSITY R&DB FOUNDATION, Seoul (KR); CHUNGBUK NATIONAL UNIVERSITY INDUSTRY-ACADEMIC COOPERATION FOUNDATION, Cheongju-si (KR)

( * ) Notice: Subject to any disclaimer, the term of this patent is extended or adjusted under 35 U.S.C. 154(b) by 0 days.

(21) Appl. No.: 17/965,456

(22) Filed: Oct. 13, 2022

(65) Prior Publication Data
US 2023/0129952 A1    Apr. 27, 2023

(30) Foreign Application Priority Data

Oct. 21, 2021    (KR) ......................... 10-2021-0140694

(51) Int. Cl.
*A01G 7/04*    (2006.01)
*H05B 47/105*    (2020.01)

(52) U.S. Cl.
CPC ........... *A01G 7/045* (2013.01); *H05B 47/105* (2020.01)

(58) Field of Classification Search
CPC .... A01G 7/045; A01G 9/249; G01N 33/0098; G01N 2021/8466; G06F 30/20; G06F 2111/10; G06Q 50/02; G06T 17/20
See application file for complete search history.

(56) References Cited

U.S. PATENT DOCUMENTS

| 11,375,595 B2* | 6/2022 | Barber | .................. A01G 7/045 |
| 11,547,062 B2* | 1/2023 | Oh | ......................... A01G 7/045 |

(Continued)

FOREIGN PATENT DOCUMENTS

| JP | 4280835 | 6/2009 |
| KR | 20150076838 | 7/2015 |
| KR | 20190122456 | 10/2019 |

OTHER PUBLICATIONS

Kim, et al., Spatial Distributions of Secondary Metabolites and Light Interception in Kale Grown under UV-B Light at Different Growth Stages, Korean Society For Horticultural Science, vol. 38 (Suppl), Nov. 2020.

(Continued)

*Primary Examiner* — Raymond R Chai
(74) *Attorney, Agent, or Firm* — CANTOR COLBURN LLP

(57) ABSTRACT

Provided is an artificial light source setting method and an artificial light source setting system for controlling secondary metabolites of plant and provide an artificial light source setting method and an artificial light source setting system for controlling secondary metabolites of plant, which predict content of the secondary metabolites of plant by measuring a light interception amount by using a cultivation environment of plant, a three-dimensional structure model of plant, and optical simulation and set an artificial light source according thereto.

6 Claims, 30 Drawing Sheets

(56) References Cited

U.S. PATENT DOCUMENTS

| | | | |
|---|---|---|---|
| 2017/0311553 A1* | 11/2017 | Dobrinsky | A01G 9/02 |
| 2021/0068351 A1* | 3/2021 | Shur | A01G 7/045 |
| 2022/0192103 A1* | 6/2022 | Kim | H05B 47/16 |
| 2022/0256776 A1* | 8/2022 | Dupras | H05B 47/105 |
| 2022/0343593 A1* | 10/2022 | Pourreza | G06V 20/17 |

OTHER PUBLICATIONS

Yoon, et al., Quantitative Analysis of UV-B Radiation Interception and Bioactive Compound Contents in Kale by Leaf Position According to Growth Progress, Frontiers in Plant Science, vol. 12, Jul. 2021.

Yoon, et al., Quantitative Analysis of UV-B Radiation Interception in 3D Plant Structures and Intraindividual Distribution of Phenolic Contents, International Journal of Molecular Sciences, 2021, vol. 22, No. 2701.

Yoon, et al., UV-B Radiation Interception in 3D Plant Structure and Intraindividual Distribution of Phenolic Contents of Kale Exposed to Short-Term UV-B near Harvest, Korean Society For Horticultural Science, vol. 39 (Suppl I), May 2021.

* cited by examiner

*FIG. 12*

| Model | DAT | $R^2$ | Adj $R^2$ | RMSE | NRMSE (%) | p-value | Model equation |
|---|---|---|---|---|---|---|---|
| TPC | 23 | 0.63 | 0.61 | 1.23 | 17.3 | <0.001 | $M(L, U) = -5.01 + 2.72 L - 0.16 L^2 + 6.54 U$ |
| | 30 | 0.77 | 0.76 | 2.17 | 18.4 | <0.001 | $M(L, U) = -25.29 + 8.30 L - 0.44 L^2 + (4.54 L - 0.38 L^2)U$ |
| | 38 | 0.72 | 0.70 | 3.90 | 22.3 | <0.001 | $M(L, U) = -26.03 + 7.62 L - 0.31 L^2 - 73.52 U + (17.18 L - 0.80 L^2)U$ |
| | Integration | 0.83 | | 2.91 | 22.2 | | |
| TFC | 23 | 0.62 | 0.60 | 0.73 | 21.4 | <0.001 | $M(L, U) = 2.42 + 39.67 U + (-12.02 L + 0.96 L^2)U$ |
| | 30 | 0.78 | 0.77 | 1.35 | 19.6 | <0.001 | $M(L, U) = -3.38 + 4.52 L - 0.25 L^2 + (2.34 L - 0.15 L^2)U$ |
| | 38 | 0.74 | 0.73 | 2.16 | 23.3 | <0.001 | $M(L, U) = -12.23 + 3.80 L - 0.16 L^2 - 47.53 U + (10.88 L - 0.49 L^2)U$ |
| | Integration | 0.83 | | 1.65 | 23.5 | | |

METHOD AND SYSTEM FOR SETTING ARTIFICIAL ULTRAVIOLET ILLUMINATION FOR PLANT

1. TECHNICAL FIELD

Embodiments of the present disclosure relate to a method and a system for setting artificial ultraviolet illumination to control secondary metabolites of plant, and more specifically, to a method and a system for controlling secondary metabolites of plant to control content of secondary metabolites of plant or cause each leaf of plant to contain uniform secondary metabolites.

2. RELATED ART

An ultraviolet ray is divided into UV-A, UV-B, and UV-C, and in a natural state, UV-C (below 280 nm) does not reach a surface of the earth due to ozone. In addition, only UV-A (320 to 390 nm) and UV-B (280 to 320 nm) having longer wavelengths than UV-C reach the surface of the earth. Accordingly, ultraviolet rays having a shorter wavelength than visible light and having high energy may damage deoxyribonucleic acid (DNA) or proteins of plant and may cause reactive oxygen species (ROS).

Therefore, secondary metabolites, such as phenol and flavonoid compounds, are accumulated in plant as one of defense mechanisms of plant against excessive ultraviolet rays. The secondary metabolites accumulated in the plant block UV rays that directly invade the plant and reduce cell damage caused by UV rays through antioxidant activity of the secondary metabolites. Accordingly, a technology capable of increasing content of secondary metabolites through low dose UV irradiation at a level that does not cause damage is being studied.

However, the known artificial UV irradiation technology uses a light source using mercury and metal halide, and thus, there is a problem in that applicability to plant is low due to a wide wavelength band and uncontrolled high energy.

In addition, a plant factory for cultivating plant is plant production facility that may optimize a cultivation environment of crops by controlling various environmental factors for cultivating plant, such as light intensity, photoperiod, temperature, and humidity. Among plant factories, artificial light-using plant factory mainly produces small leafy vegetables by using light emitting diodes (LEDs).

However, LEDs for plant cultivation used in the general plant factory are designed only for the purpose of promoting growth of crops with uniform light distribution and efficient intensity and may not be used for increasing and controlling content of bioactive materials (secondary metabolites) of plant.

When the content of secondary metabolites of plant is controlled, or when the secondary metabolites are not uniformly contained in plant, non-uniformity in quality may occur in functional plant derived from natural products or medicinal products derived from natural products.

In addition, response of plant to ultraviolet rays is affected by not only intensity of the ultraviolet rays but also physiological factors such as leaf age. Accordingly, accumulation of content of bioactive materials in plant is also affected by bioactive factors such as leaf age. However, the plant has a three-dimensional structure in which positions of leaves having various leaf ages are mixed, and thus, it is difficult to predict content of secondary metabolites of plant when the known LEDs for plant cultivation for simply irradiating uniform light are used.

SUMMARY

Embodiments of the present disclosure provide a method and a system for setting artificial ultraviolet illumination to increase content of secondary metabolites of plant and uniformize content of secondary metabolites contained in each leaf of plant.

However, technical tasks to be achieved by the present embodiment is not limited to the technical task described above, and other technical tasks may exist.

According to an aspect of the present disclosure, an artificial light source setting method includes generating a simulation model by using a three-dimensional structure model of the plant and light source data of a plant factory, predicting content of secondary metabolites of each of a plurality of leaves by analyzing light interception of each of the plurality of leaves included in the three-dimensional structure model of the plant, and deriving a light source setting value such that the content of secondary metabolites of each of the plurality of leaves has a preset value, and changing an artificial light source setting of the plant factory according to the light source setting value.

In addition, according to an embodiment, the generating of the simulation model may include generating three-dimensional scan data of the plant by using a three-dimensional scanner and generating a surface model by using the three-dimensional scan data.

In addition, according to an embodiment, the predicting of the content of secondary metabolites may include setting each of the plurality of leaves included in the surface model as a detector and predicting a light interception amount of each of the plurality of leaves of the plant.

In addition, according to an embodiment, the predicting of the content of secondary metabolites may further include receiving data on optical properties and the content of secondary metabolite of the plant and performing linear regression analysis on the optical properties and the content of secondary metabolites of the plant.

In addition, according to an embodiment, the predicting the content of secondary metabolites may further include deriving the light interception amount according to any one of each leaf of the plant and a growth stage of the plant by using a prediction result of the light interception amount for each leaf, and predicting the content of secondary metabolites by using the light interception amount according to any one of each leaf of the plant and the growth stage of the plant and a result of the linear regression analysis.

According to another aspect of the present disclosure, an artificial light source setting system includes an artificial ultraviolet light source configured to generate light for cultivation of plant, a memory in which an optical simulation program is stored, and a processor configured to execute an optical simulation program stored in the memory, wherein the processor executes the optical simulation program to generate a simulation model by using a three-dimensional structure model of the plant and light source data of a plant factory, predicting content of secondary metabolites of each of a plurality of leaves by analyzing light interception of each of the plurality of leaves included in the three-dimensional structure model of the plant, and deriving a light source setting value such that the content of secondary metabolites of each of the plurality of leaves has a preset value, and the artificial light source is controlled according to the light source setting value.

Embodiments of the present disclosure may provide a method and a system for setting artificial ultraviolet illumination to increase content of secondary metabolites of plant and uniformize content of secondary metabolites contained in each leaf of plant.

BRIEF DESCRIPTION OF THE DRAWINGS

FIG. 12 is a table illustrating parameters of a model equation for secondary metabolite content prediction using an ultraviolet light interception amount depending on growth stages of plant;

DETAILED DESCRIPTION OF THE EMBODIMENTS

Figure 1:
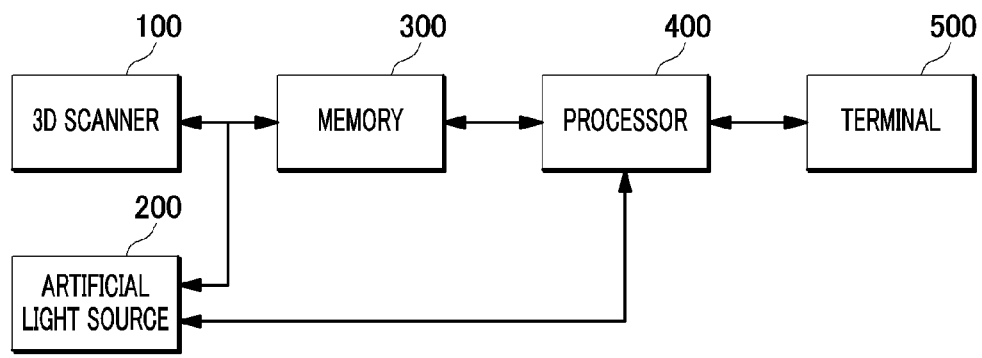
FIG. 1 is a block diagram of an artificial ultraviolet illumination setting system for controlling secondary metabolites of plant, according to an embodiment of the present disclosure.

Hereinafter, embodiments of the present disclosure will be described in detail with reference to the accompanying drawings such that those skilled in the art may easily implement the embodiments. However, the present disclosure may be embodied in several different forms and is not limited to the embodiments described herein. In order to clearly describe the present disclosure in the drawings, parts irrelevant to the description are omitted, and similar reference numerals are attached to similar components throughout the specification.

Throughout the specification, when a portion is "connected" or "coupled" to another portion, this includes not only a case of being "directly connected or coupled" but also a case of being "electrically connected" with another element interposed therebetween. In addition, when a portion "includes" a certain component, this means that other components may be further included therein rather than excluding other components, unless otherwise stated.

In the present specification, a term "system" includes a unit implemented by hardware, a unit implemented by software, and a unit implemented by both. In addition, one unit may be implemented by two or more pieces of hardware, and two or more units may be implemented by one piece of hardware. Meanwhile, the "unit" is not limited to software or hardware, and the "unit" may also be configured to be included in an addressable storage medium or to reproduce one or more processors. Accordingly, for example, the "unit" includes components such as software components, object-oriented software components, class components, and task components, processes, functions, properties, procedures, subroutines, segments of program code, drivers, firmware, microcode, circuitry, data, databases, data structures, tables, arrays, and variables. Functions provided in components and "units" may be combined with a smaller number of components and "units" or may be further separated into additional components and "units". In addition, components and "units" may also be implemented to reproduce one or more CPUs in a device.

In addition, the accompanying drawings are only for easy understanding of the embodiments disclosed in the present specification, and the technical idea disclosed herein is not limited by the accompanying drawings, and should be understood to include all changes, equivalents, or substitutes included in the idea and scope of the present disclosure.

Terms including an ordinal number, such as first, second, and so on may be used to describe various components, but the components are not limited by the terms. The above terms are used only for the purpose of distinguishing one component from another component.

When it is described that a component is "connected" or "coupled" to another component, it should be understood that the component may be directly connected or coupled to another component, but other components may exist therebetween. Meanwhile, when it is described that a certain component is "directly connected" or "directly coupled" to another component, it should be understood that other elements do not exist therebetween.

The singular expression includes the plural expression unless the context clearly dictates otherwise.

In the present application, terms such as "include" or "have" are intended to designate that there are features, numbers, steps, operations, configuration elements, component, or combinations thereof described in the specification, and it should be understood that the present disclosure does not preclude possibility of addition or existence of one or more other features, numbers, steps, operations, configuration elements, components, or combinations thereof.

Hereinafter, a configuration of an artificial ultraviolet illumination setting system 1 for controlling secondary metabolites of plant, according to an embodiment will be described with reference to FIG. 1.

FIG. 1 is a configuration diagram of an artificial ultraviolet illumination setting system for controlling secondary metabolites of plant, according to an embodiment.

Referring to FIG. 1, the artificial ultraviolet illumination setting system 1 for controlling secondary metabolites of plant uses three-dimensional (3D) scan data and light source data of plants to control secondary metabolites of plant. The artificial ultraviolet illumination setting system 1 generates three-dimensional scan data of plants by using a 3D scanner 100.

For example, 3D scan data of plants may be acquired by using a high-resolution portable 3D scanner such as Go!scan (Go!scan50™) and scan software such as Vxelemnet and Creaform. The 3D scan data acquired by using the 3D scanner 100 may include information on a size, a shape, a height, an arrangement position, and so on for each leaf.

In this case, the 3D scanner 100 is used to generate a 3D model of plant. Therefore, the present disclosure does not generate a 3D structure model of plant by using the scan data acquired by using the 3D scanner 100 but may also use a method of inputting a specific value by a user or randomly generating a 3D structural model of a specific shape.

In addition, light source data of the artificial light source 200 may include all types of information on a light source, such as a spectrum, a light distribution, and shape of the light source. In addition, the light source data may be acquired by using setting information of the artificial light source 200 and measuring optical properties directly irradiated to the plant.

In this case, the optical properties of the artificial light source 200 measured to input light source data similar to actual cultivation environment. Accordingly, a user may set any light source data without measuring the optical properties.

The memory 300 stores an optical simulation program. The optical simulation program is set for the sake of convenience of description, and the name itself does not limit functions of the program. The memory 300 may store at least one of data generated or measured by the 3D scanner 100 and the artificial light source 200, information and data necessary for a function performed by a processor 400, and data generated according to the processor 400.

The memory 300 may include a non-volatile storage device that continuously maintains stored information even when power is not supplied, and a volatile storage device that requires power to maintain the stored information. In addition, the memory 300 may perform a function of temporarily or permanently storing data processed by the processor 400.

The memory 300 may include magnetic storage media or flash storage media in addition to a volatile storage device that requires power to maintain stored information, but the scope of the present disclosure is not limited thereto.

In addition, the artificial ultraviolet illumination setting system 1 for controlling secondary metabolites of plant may further include a database (not illustrated). The database may store data required to perform optical simulations. For example, the database may include result accumulation data of an optical simulation program, big data for learning of the optical simulation program, light interception analysis data according to a height of a leaf and a light source, light interception analysis data according to growth stage of plant and a light source, secondary metabolite content data according to a height of a leaf and a light source, secondary metabolite content data according to growth stage of plant, and so on. The database may constitute a part of the memory 300 but may also be located at the outside of the artificial ultraviolet illumination setting system 1 without being located at the inside thereof.

The processor 400 is configured to execute an optical simulation program stored in the memory 300. The processor 400 may include various types of devices for controlling and processing data. The processor 400 may refer to a data processing device that is embedded in hardware and has a physically structured circuit to perform a function represented as a code or an instruction included in a program. In one example, the processor 400 may be implemented by a microprocessor, a central processing unit (CPU), a processor core, a multiprocessor, an application-specific integrated circuit (ASIC), or a field programmable gate array (FPGA), but the scope of the present disclosure is not limited thereto.

The processor 400 executes an optical simulation program to perform following functions and procedures.

The processor 400 analyzes a light interception amount according to a light source and content of secondary metabolites by 3D-modeling plant cultivation environment (a plant factory) and a shape of plant. To this end, a 3D structure model and a surface model of plant may be generated by using the 3D scan data acquired by the 3D scanner 100.

In addition, a simulation environment may be built by using a 3D structure model, a surface model, and light source data of plant. The simulation environment may be generated by using a computer aided design (CAD) program as well as a method using an optical simulation program.

In the simulation environment, a plant factory model may be generated by using a cultivation environment in a plant factory and light source data used for plant cultivation, and a 3D structural model or a surface model of plant generated by using 3D scan data may be arranged. In addition, after all leaf models included in the 3D structure model or the surface model of the plant are set by a detector, optical simulation may be performed.

As a result of the optical simulation, light interception analysis on each of a plurality of leaves may be performed, and content of secondary metabolites of each of the plurality of leaves may be predicted. In addition, the optical simulation program may change a light source setting value of a simulation environment to have a set target content of secondary metabolites.

Therefore, content of secondary metabolites of plant may be adjusted by applying the changed light source setting value of the simulation environment to an actual plant factory. However, the present disclosure is not limited to changing the light source setting and may include changing various data for generating a plant factory model and changing setting of a plant factory according thereto.

In addition, the processor 400 may change a vertical distance, a horizontal interval, and a side irradiation angle of a light source included in a simulation model and may predict an ultraviolet light interception amount and content of secondary metabolites for each leaf of the plant according thereto. In addition, setting of a light source may be changed by using an ultraviolet light interception amount and content of secondary metabolites for each leaf according to the vertical distance, the horizontal interval, and the side irradiation angle of the light source.

Details of a simulation method and a setting change method will be described with reference to FIGS. 2 to 5 described below.

In addition, a setting value derived by the processor 400 that executes an optical simulation program may be transmitted to a plant factory by using a communication unit (not illustrated), and the plant factory may change setting of a light source of the plant factory by using the received setting value.

In addition, the processor 400 may transmit and receive information to and from a terminal 500 by using the communication unit. Accordingly, the processor 400 may receive an environment setting value of a simulation model from the terminal 500 or transmit an optical simulation program execution result to the terminal 500, thereby displaying the information to a user.

The terminal 500 may refer to, for example, a notebook computer storing a web browser, a desktop computer, a laptop computer, a mobile wireless communication device, or a handheld-based wireless communication device such as a smartphone or a tablet personal computer (PC). In addition, the communication network may be implemented by a wired network, such as a local area network (LAN), a wide area network (WAN), or a value added network (VAN), or all types of wireless networks, such as a mobile radio communication network or a satellite communication network.

Hereinafter, an artificial ultraviolet illumination setting method for controlling secondary metabolites of plant, according to an embodiment will be described with reference to FIG. 2.

Figure 2:
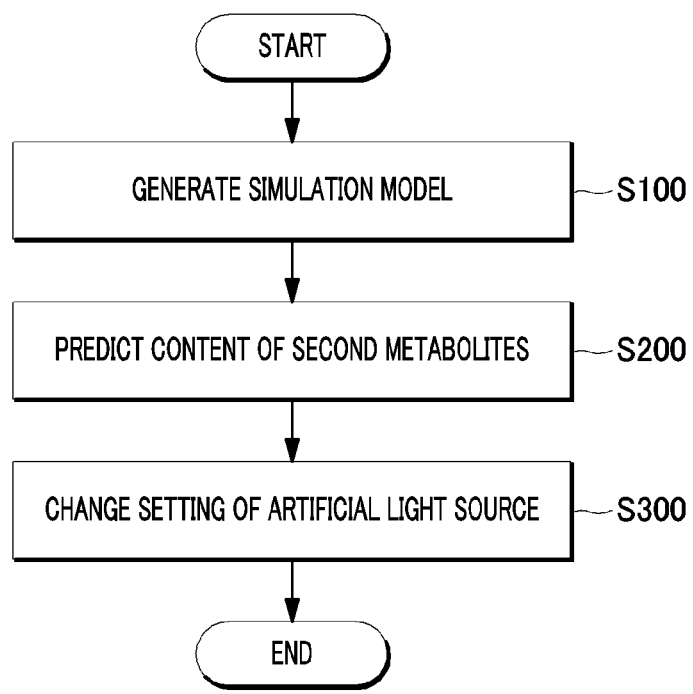
FIG. 2 is a flowchart of an artificial ultraviolet illumination setting method for controlling secondary metabolites of plant, according to an embodiment of the present disclosure.

FIG. 2 is a flowchart of an artificial ultraviolet illumination setting method for controlling secondary metabolites of plant, according to an embodiment.

Referring to FIG. 2, the processor 400 may execute an optical simulation program to perform a simulation model generation step S100, a secondary metabolite content prediction step S200, and an artificial light source setting change step S300.

In the simulation model generation step S100, a simulation model identical to plant cultivation environment is generated by using a 3D structure model of plant and light source data. Accordingly, the simulation model includes a 3D plant factory model having the same size and intensity a light source as an actual plant factory cultivation environment.

In order to generate a 3D structure model of plant, a method of using scan data acquired by the 3D scanner 100 as described above and a method of generating a 3D structure model of plant by inputting a specific value by a user or randomly generating a 3D structure model of a specific shape may be used.

Description of a surface model will be made with reference to FIGS. 3 and 4 to be described below.

In addition, in the simulation model generation step S100, a surface model of plant may be generated by using 3D scan data of plant. A method of generating the surface model will be described in detail with reference to FIGS. 3 and 4 to be described below.

Setting information of the artificial light source 200 may be used to acquire light source data, and the light source data may be acquired by directly measuring optical properties irradiated to plant. However, the present disclosure is not limited thereto, and a user may set any light source data.

In the secondary metabolite content prediction step S200, optical simulation on a simulation model is performed to analyze light interception on each leaf of plant and to measure a light interception amount and to predict content of secondary metabolites according thereto.

In this case, in order to perform the optical simulation, a light interception amount according to a height of a leaf and a growth stage of the plant may be simulated, and thereby, content of secondary metabolites may be predicted. A specific method of predicting the content of secondary metabolites will be described in detail with reference to FIG. 5 to be described below.

In addition, in the secondary metabolite content prediction step S200, a vertical distance, a horizontal interval, and a side irradiation angle of a light source included in the simulation model may be changed, and an ultraviolet light interception amount and content of secondary metabolites for each leaf of plant may be predicted according thereto.

In the artificial light source setting change step S300, target content of secondary metabolites on content of secondary metabolites of plant is set, and a light source setting value corresponding thereto is derived. In addition, an actual plant may have the target content of secondary metabolites by changing setting of an artificial light source of a plant factory according to the light source setting value.

In this case, the target content of secondary metabolites may indicate not only the total content of secondary metabolites of plant but also uniform content of secondary metabolites of each leaf. In addition, in order to derive a light source set value of an artificial light source, the light source set value may be derived by using a results of linear regression analysis on the light interception amount and the content of secondary metabolites described above.

Specifically, the light interception amount is changed according to light source data, and the content of secondary metabolites of plant is changed according to the light interception amount. Accordingly, a first relation equation on the light source data and the light interception amount may be derived by using the result of light interception amount analysis according to the light source data of a simulation model. In addition, a second relation equation on the light interception amount and the content of secondary metabolites may be derived by using linear regression analysis results on the light interception amount and the content of secondary metabolites described above.

Therefore, a third equation on light source data and content of secondary metabolites may be derived by using the first relation equation on the light source data and the light interception amount and the second relation equation on the light interception amount and the content of secondary metabolites. Accordingly, the light source data for deriving the target content of secondary metabolites may be extracted by substituting a target secondary metabolite content value into the third equation. That is, a target light interception amount corresponding to the target content of secondary metabolites is derived, and light source data corresponding to the target light interception amount is derived as a light source setting value.

In addition, it is also possible to use a method of deriving light source data close to target content of secondary metabolites as a light source setting value by predicting content of secondary metabolites according to a plurality of pieces of light source data set by a user.

Hereinafter, the simulation model generation method S100 according to an embodiment will be described with reference to FIGS. 3 and 4.

Figure 3:
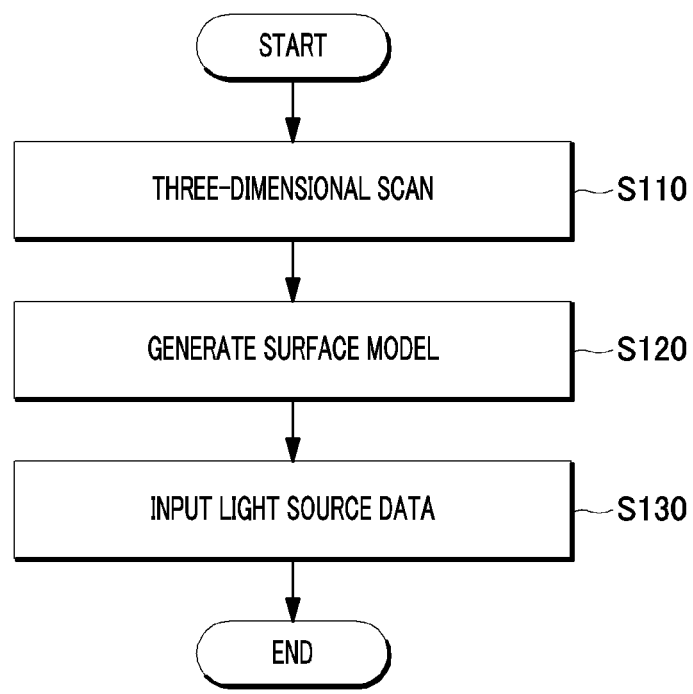
FIG. 3 is a flowchart of a simulation model generation method according to an embodiment of the present disclosure.

FIG. 3 is a flowchart of the simulation model generation method according to the embodiment.

Figure 4:
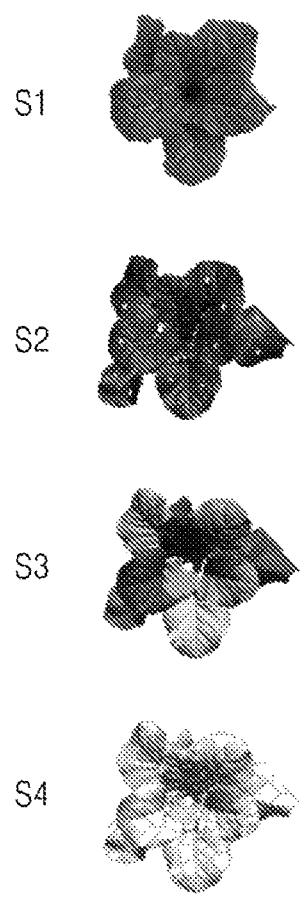
FIG. 4 illustrates example views of a three-dimensional structure model of plant according to an embodiment of the present disclosure.

FIG. 4 illustrates views of a 3D structure model of plant, according to an embodiment.

Referring to FIG. 3, in a 3D scan step S110, plant is scanned by the 3D scanner 100. Accordingly, 3D scan data of plant may be acquired. In a surface model generation step S120, a surface model is generated by using the acquired scan data. The surface model may correspond to a 3D structure model of plant.

Specifically, 3D scan data of plant is acquired by using the 3D scanner 100 and scan software. The acquired 3D scan data may correspond to 3D mesh data. Noise and holes may be segmented and corrected by using the 3D mesh data to be segmented into leaf mesh data for each leaf. The segmented leaf mesh data may be reconfigured as a surface model for being applied to light tracing simulation by using reverse engineering software such as Geomagic Design X.

FIG. 4 illustrates examples of a 3D structure model of plant. S1 corresponds to kale, which is an actual plant, and S2 corresponds to mesh data generated by scanning S1 with the 3D scanner 100. That is, S2 may correspond to 3D scan data of the plant S1.

S3 may correspond to leaf mesh data for distinguishing each leaf as a form that has undergone segmentation correction on the 3D scan data S2. S4 corresponds to a surface model generated to be applied to the light tracing simulation through reconstruction.

In the light source data input step S130, data corresponding to light source properties of an artificial light source such as an ultraviolet (UV) light emitting diode (LED) is input. The light source properties may include information on a spectrum, a light distribution, and a shape of a light source.

In addition, the light source data input step S130 may include a step of generating a 3D model of a plant factory. A 3D structure model or a surface model of plant may be transferred to 3D computer-aided design (CAD) software such as Solidworks and may be placed on a 3D model of a plant factory.

Therefore, the 3D model of the plant factory may indicate that a structure of the plant factory is generated as a 3D model by using not only an artificial light source but also data related to the structure of the plant factory and the plant factory.

In addition, the simulation model may include a simulation model in which Light source data is applied to the three-dimensional structural model of the plant and a 3D structure model of plant is placed in a 3D model of a plant factory generated in the light source data input step S130.

Hereinafter, the secondary metabolite content prediction method S200 according to an embodiment will be described with reference to FIG. 5.

Figure 5:
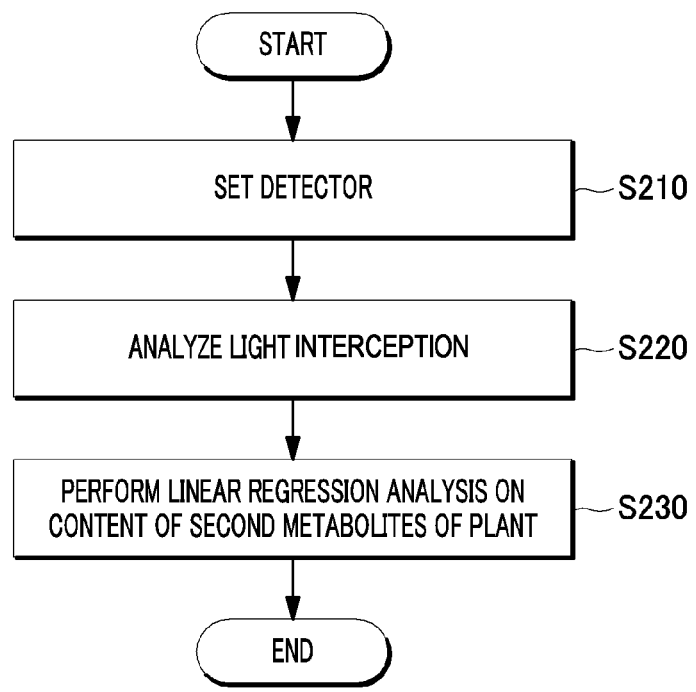
FIG. 5 is a flowchart of a secondary metabolite content prediction method according to an embodiment of the present disclosure.

FIG. 5 is a flowchart of the secondary metabolite content prediction method according to the embodiment.

Referring to FIG. 5, in a detector setting step S210, each of a plurality of leaves included in the surface model is set as a detector.

In a light interception analysis step S220, light interception analysis is performed by using an optical simulation program such as Optisworks. By setting each leaf as a detector in the detector setting step S210, a light interception amount of each leaf may be measured. That is, the light interception amount of each leaf according to light source data may be predicted by using the optical simulation program.

In addition, in the light interception analysis step S220, not only the light interception amount of each leaf but also light interception amounts according to height of leaves and a light interception amount depending on growth stages of plant may be derived.

Leaves of plant are not arranged regularly but have different structures for each plant. Accordingly, plant may have different leaves in a position, a height, a size, a growth stage, and so on. Accordingly, by measuring and analyzing a light interception amount for each leaf, the light interception amount of plant may be predicted more accurately.

First, the oldest leaf at the bottom to the newest leaf at the top are numbered according to height, and then light interception amounts of the leaves are measured.

Heights of leaves are divided into top, middle, and bottom based on the lowest leaf and the highest leaf in a three-dimensional structural model of plant, and a light interception amount for each height of leaf may be derived by summing light interception amounts of leaves located in each height. In this case, the embodiment of the present disclosure is not limited to dividing a height into three sections of upper, middle, and lower, and may include analysis of the light interception amounts according to height by segmenting a height into a plurality of sections of three or more.

In addition, in order to measure the light interception amounts according to growth stage, a 3D structure model of plant corresponding to a growth period of plant may also be changed. Accordingly, the light interception amounts according to growth stage may be measured by dividing a growth period of plant into a plurality of sections and performing light interception analysis on a 3D structure model of plant corresponding to each growth section.

In addition, the growth stage may include not only points in time from germination of plant to cultivation thereof but also any period set by a user, such as a specific period before plants are harvested.

In a linear regression analysis step S230 on optical properties and content of secondary metabolites of plant, linear regression analysis is performed to derive a first relation equation on a light interception amount and content of secondary metabolites, and a predicted value (analysis value) of the light interception amount is substituted into the first relation equation, and thus, the content of secondary metabolites may be predicted.

For example, before harvesting kale grown in a plant factory, a UV LED (an artificial light source) is irradiated for 12 hours a day for two days to measure a light interception amount of kale and content of secondary metabolites according thereto. In addition, an optical simulation program may derive a first relation equation on a light interception amount and secondary metabolites by performing a linear regression analysis on the measured light amount and secondary metabolite content data.

That is, a light interception amount, content of secondary metabolites, and optical properties of plant are measured for an actual plant, and a relation equation on the light interception amount and secondary metabolites is derived using the light interception amount, the content of secondary metabolites, and the optical properties. In addition, the content of secondary metabolites may be predicted by substituting the predicted light interception amount into the first relational expression.

Hereinafter, optical properties of plant will be described with reference to FIGS. 6 and 7.

Figure 6:
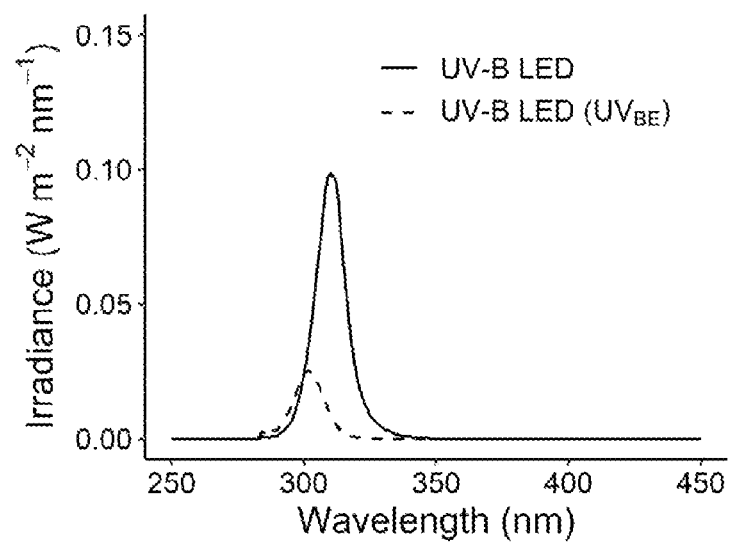
FIG. 6 is a spectrum graph of an artificial light source.

FIG. 6 is a spectrum graph of artificial ultraviolet light source (an artificial light source).

Referring to FIG. 6, FIG. 6 is an example of a spectrum graph of a UV-B LED is illustrated.

The UV-B LED may generate light having a wavelength in the range of 250 nm to 400 nm corresponding to ultraviolet light. In addition, the UV-B LED may have a spectral peak at about 310 nm, and the irradiance may be set to 3.0 Wm-2 at 7 cm above the center of a floor. Spectra and intensities of photosynthetic active radiation (PAR) and an UV-B LED may be measured by using a spectroradiometer (BlueWave Spectrometer, StellarNet Inc., Tampa, FL, United States) in the range of 250 nm to 900 nm.

Figure 7:
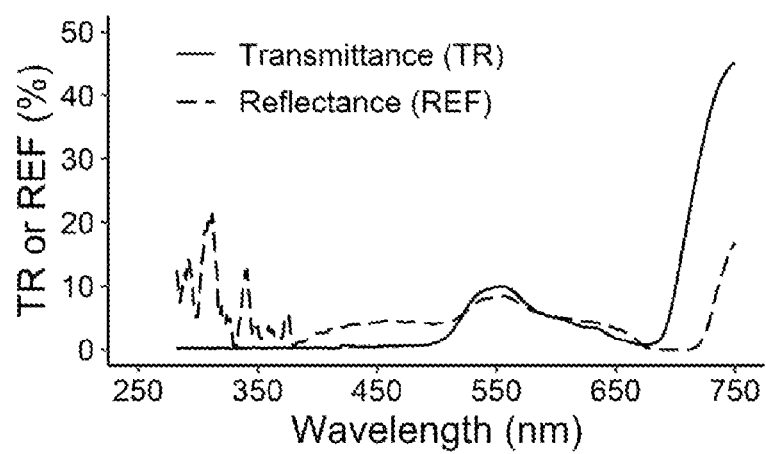
FIG. 7 is a graph illustrating optical properties of kale.

FIG. 7 is a graph of optical properties of kale.

Referring to FIG. 7, graphs on transmittance and reflectance among optical properties of kale are illustrated as an example to describe optical properties of a leaf. FIG. 7 illustrates graphs of transmittance and reflectance measured by irradiating kale with light from a cultivation light source and the UV-B LED.

TR is a graph of transmittance measured by irradiating kale with light from an artificial light source. REF is a graph of reflectance measured by irradiating kale with light from the artificial light source. The transmittance and reflectance are only some examples of optical properties of kale, and other optical properties may be used depending on an analysis purpose and an artificial light source setting purpose.

The spectral properties of an artificial light source and the optical properties of plant described above may be used to measure a light interception amount and predict content of secondary metabolites according thereto by performing optical simulation on a simulation model and analyzing light interception on each leaf of plant.

Hereinafter, examples of a light interception analysis result of plant surface according to a growth stage of plant by using a 3D structure model will be described with reference to FIGS. 8A to 8C.

Figure 8A:
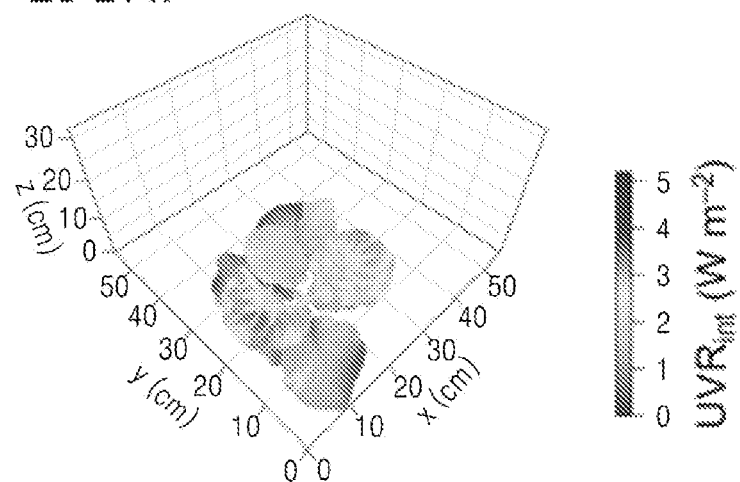
FIGS. 8A, 8B, and 8C are diagrams illustrating light interception analysis of plant surface during ultraviolet (UV) irradiation.
Figure 8B:
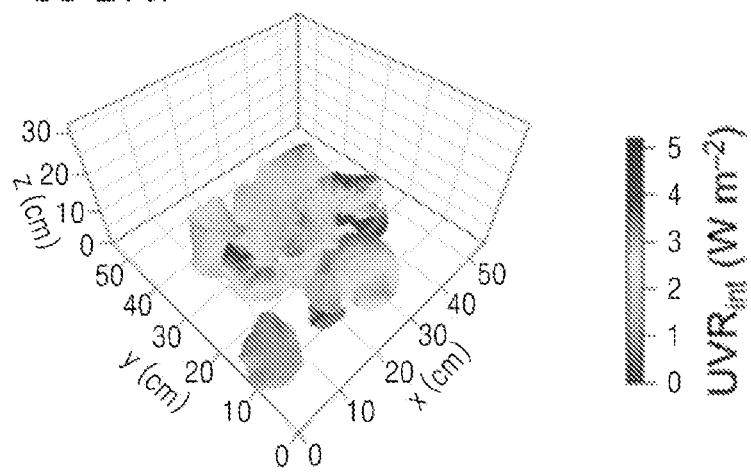
Figure 8C:
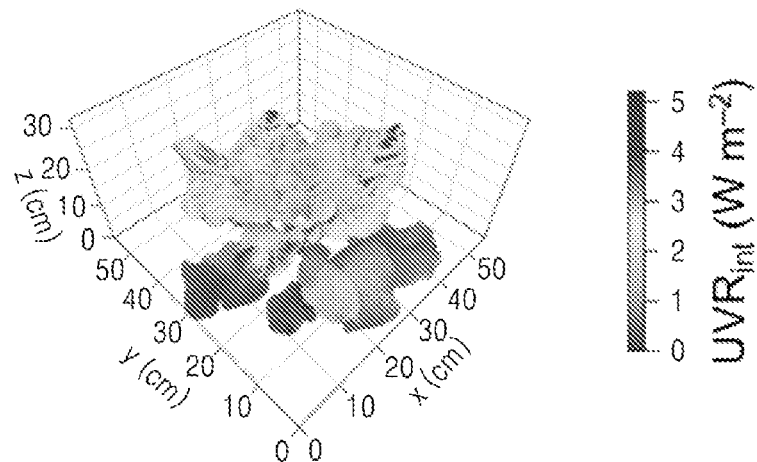

FIGS. 8A, 8B and 8C are diagrams illustrating light interception analysis according to growth stage of plant.

FIGS. 8A, 8B and 8C illustrate light interception analysis results derived by performing optical simulation in an ultraviolet (UV, 250 nm to 400 nm) region. FIG. 8A illustrates a UV absorption amount of plant model on the 23rd day after transplantation, FIG. 8B illustrates a UV absorption amount of plant model on the 30th day after transplantation, and FIG. 8C illustrates a UV absorption amount of plant model on the 38th day after transplantation.

As illustrated in FIGS. 8A, 8B and 8C, light interception analysis result may be visually displayed together with a 3D structure model including a height, an angle, and a surface curvature of a leaf.

In addition, the light interception analysis result may be quantified for each leaf.

Hereinafter, an example of the light interception analysis result of the 3D structure model will be described with reference to FIG. 9.

Figure 9:
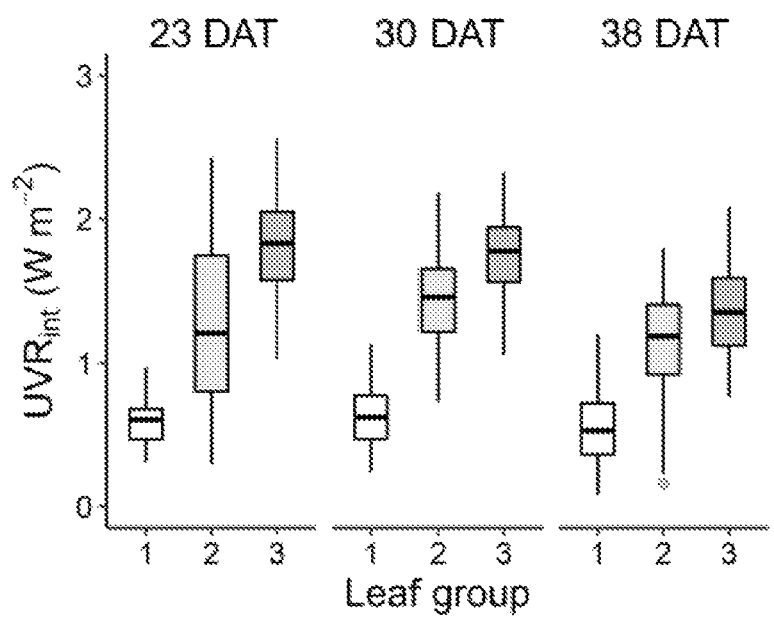
FIG. 9 is a graph illustrating a light interception distribution for each leaf.

FIG. 9 is a graph illustrating a light interception distribution according to growth stage of plant and for each leaf position.

referring to FIG. 9, simulation results in plant exposed to a cultivated light source and a UV-B LED are illustrated.

A growth stage of plant may be divided into the 23rd day (23DAT), the 30th day (30DAT), and the 38th day (38DAT). The leaf group corresponds to an order according to heights from the lowest leaf to the highest leaf of kale. In this case, leaves of a first group located at the lowermost may correspond to the oldest leaves, and leaves of a third group located at the uppermost may correspond to the youngest leaves. Accordingly, groups and heights of the leaves may correspond to ages of the leaves. In addition, mid-age leaves located at a mid-height may be classified into a second group.

A distribution of light interception for each leaf may be illustrated by using violin plots based on kernel density estimation and box plots.

Examples of a light interception analysis result of the 3D structural model will be described with reference to FIGS. 10A to 10C.

Figure 10A:
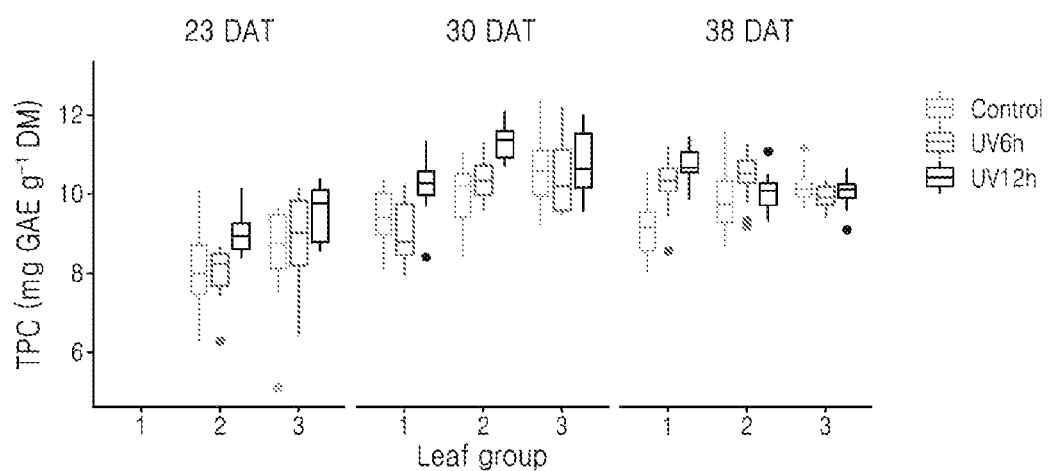
FIGS. 10A, 10B, and 10C are graphs illustrating content of secondary metabolites and antioxidant activity analysis.
Figure 10B:
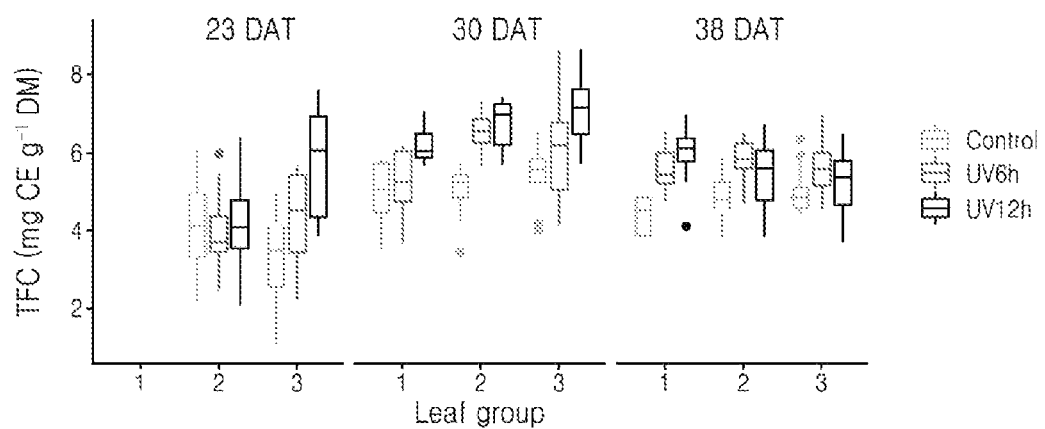
Figure 10C:
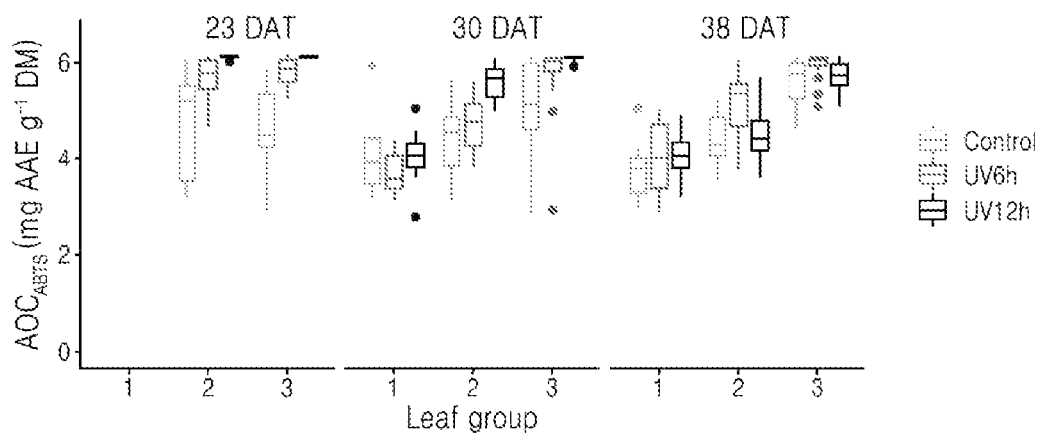

FIGS. 10A, 10B, and 100 are graphs illustrating content of secondary metabolite and antioxidant activity analysis according to growth stage and leaf location.

FIGS. 10A to 100 are graphs illustrating content of secondary metabolites of kale when a UV-B is irradiated and illustrate analysis results according to flavonoids, phenolic compounds, and antioxidant activity. FIG. 10A illustrates total phenolic content (TPC), FIG. 10B illustrates total flavonoid content (TFC), and FIG. 100 illustrates antioxidant activity using ABTS (AOCABTS).

Control represents a case in which no UV treatment is applied, UV6h represents a case in which plant is exposed to UV-B for six hours before harvest, and UV12h represents a case in which plant is exposed to UV-B for 12 hours before harvest.

Hereinafter, a relationship between an ultraviolet light interception value and content of secondary metabolites and a regression analysis result will be described with reference to FIGS. 11A and 11B.

Figure 11A:
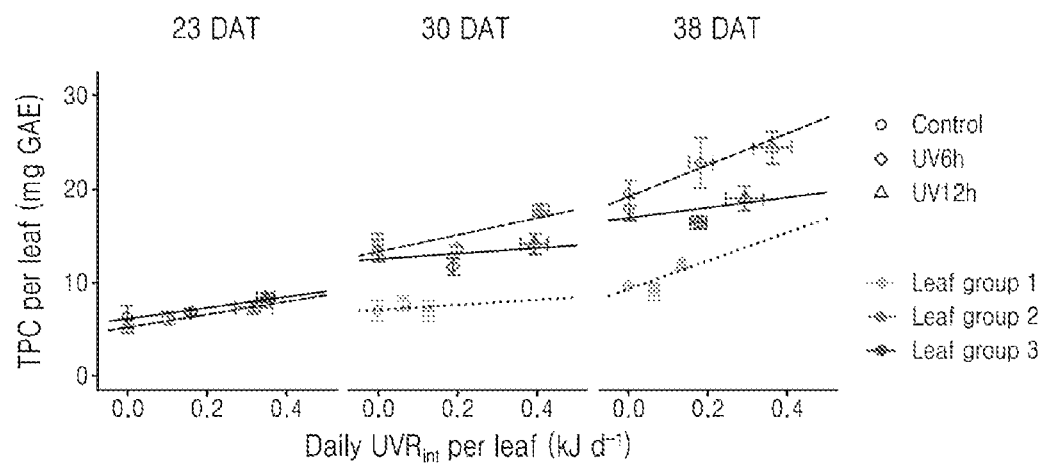
FIGS. 11A and 11B are graphs illustrating an ultraviolet light interception amount depending on growth stages and leaf positions, content of secondary metabolites, and antioxidant activity analysis.
Figure 11B:
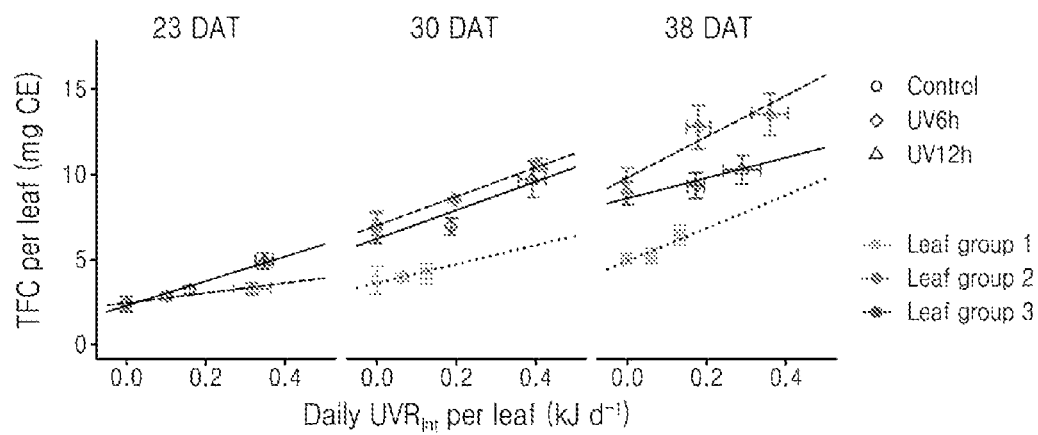

FIGS. 11A and 11B are graphs illustrating linear regression analysis of an ultraviolet light interception amount and phenol and flavonoid contents according to growth stage and leaf position.

FIG. 11A illustrates total phenolic compound content according to an ultraviolet light interception value, and FIG. 11B illustrates total flavonoid compound content according to the ultraviolet light interception value. FIGS. 11A and 11B may be generated by using the data of FIG. 9 and FIGS. 10A, 10B, and 100. A light interception value may be derived by performing linear regression analysis on light interception values for each leaf in FIG. 9 and data on content of bioactive compounds (flavonoid compound and phenolic compound) for each leaf and antioxidant activity result in FIGS. 10A to 100. However, a less light interception value is derived by only the linear regression analysis, and thus, the content of secondary metabolites may not be represented only by the light interception value.

As such, the processor 400 may quantitatively predict an ultraviolet light interception distribution of plant by using an optical simulation program and estimate an ultraviolet light interception value of plant by a UV LED and content of secondary metabolites according to leaf ages in plant object.

FIG. 12 is a table including parameters of a model equation for predicting content of secondary metabolites using an ultraviolet light interception amount depending on growth stages of plant.

The content of secondary metabolites of plant may be derived by Equation 1 below and an ultraviolet light interception amount depending on growth stages of plant.

$$M(L,U)=\beta_0+\beta_1 L+\beta_2 L^2+\beta_3 U+(\beta_4 L+\beta_5 L^2)U \qquad \text{Equation 1}$$

Here, M may represent a model for deriving content of secondary metabolites (mg) per leaf. L may represent an order of leaves and may be ranked according to an order of appearance of leaves. U may represent daily UV radiation protection per leaf (kJ day-1). In addition, $\beta 0$-$\beta 5$ are regression coefficients obtained through regression analysis at each growth stage and may be set differently depending on whether a model derives TPC content, whether a model derives TFC, and growth stages (23 DAT, 30 DAT, 38DAT) of plant, as illustrated in FIG. 12. In addition, all models have a highly accurate R2 value of about 0.7, as illustrated in FIG. 12.

Figure 13A:
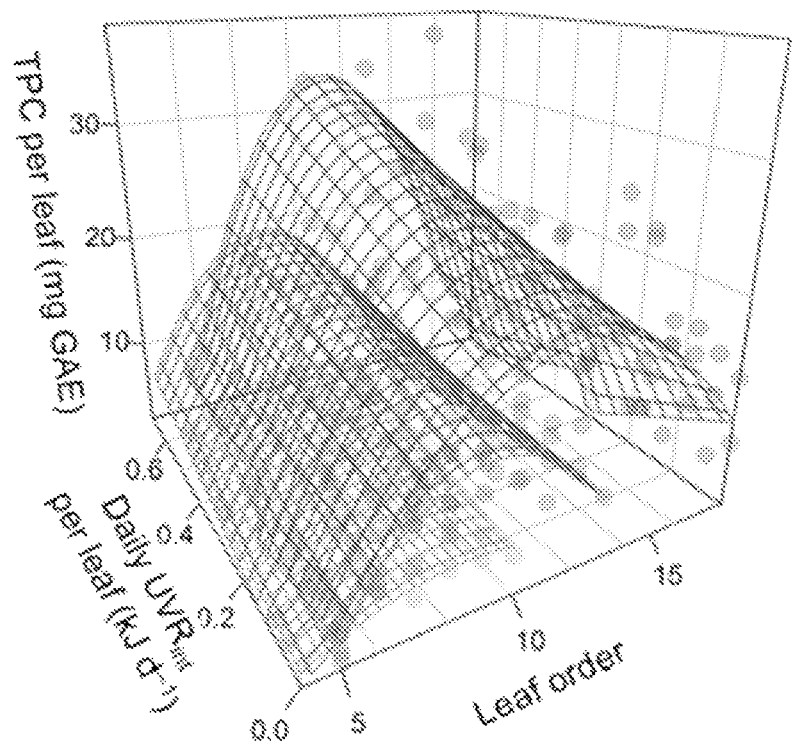
FIGS. 13A and 13B are graphs illustrating a secondary metabolite content prediction model using the ultraviolet light interception amount depending on growth stages of plant.
Figure 13B:
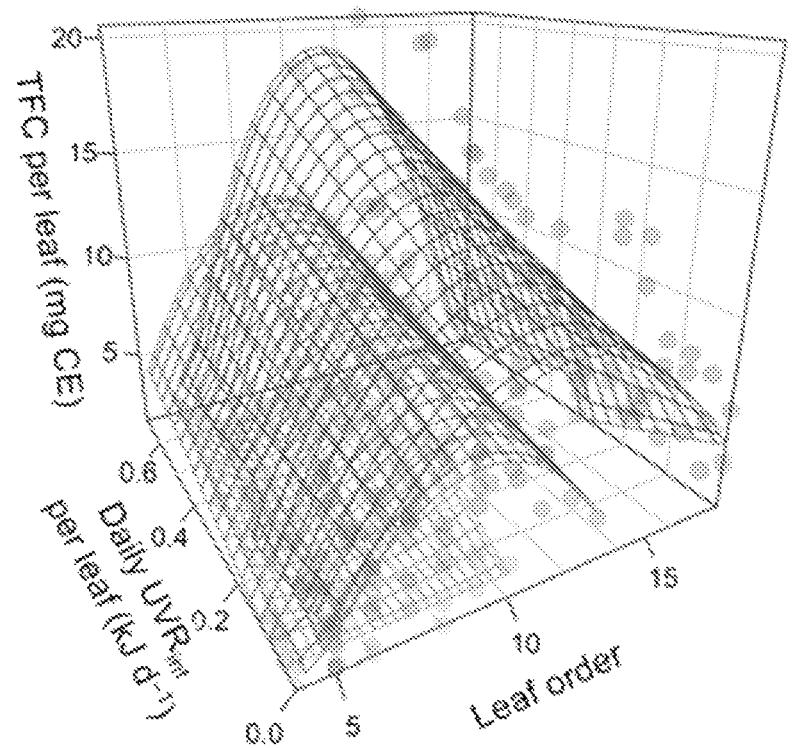

FIGS. 13A and 13B are graphs illustrating a secondary metabolite content prediction model using an ultraviolet light interception amount for each growth stage.

FIG. 13A illustrates a graph of a TPC content prediction model, and FIG. 13B illustrates a graph of a TFC content prediction model. As illustrated in FIGS. 13A and 13B, the TPC and TFC content prediction models for each growth stage may have a form of a curved surface in which light interception amounts and an order of occurrence of leaves are used as variables.

Figure 14A:
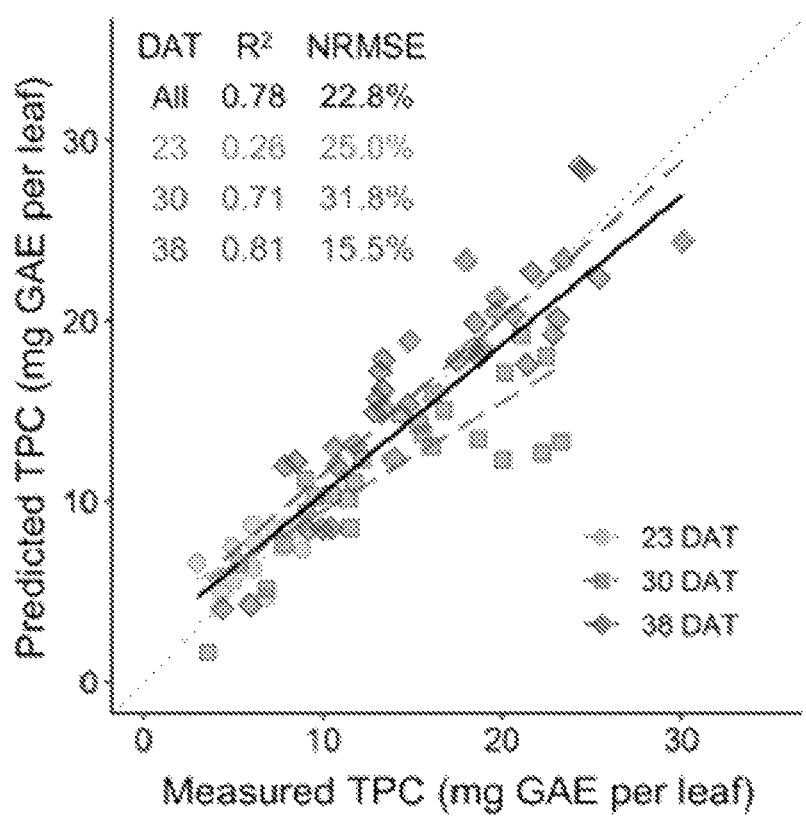
FIGS. 14A and 14B are graphs illustrating accuracy evaluation of the secondary metabolite content prediction model according to an embodiment of the present disclosure.
Figure 14B:
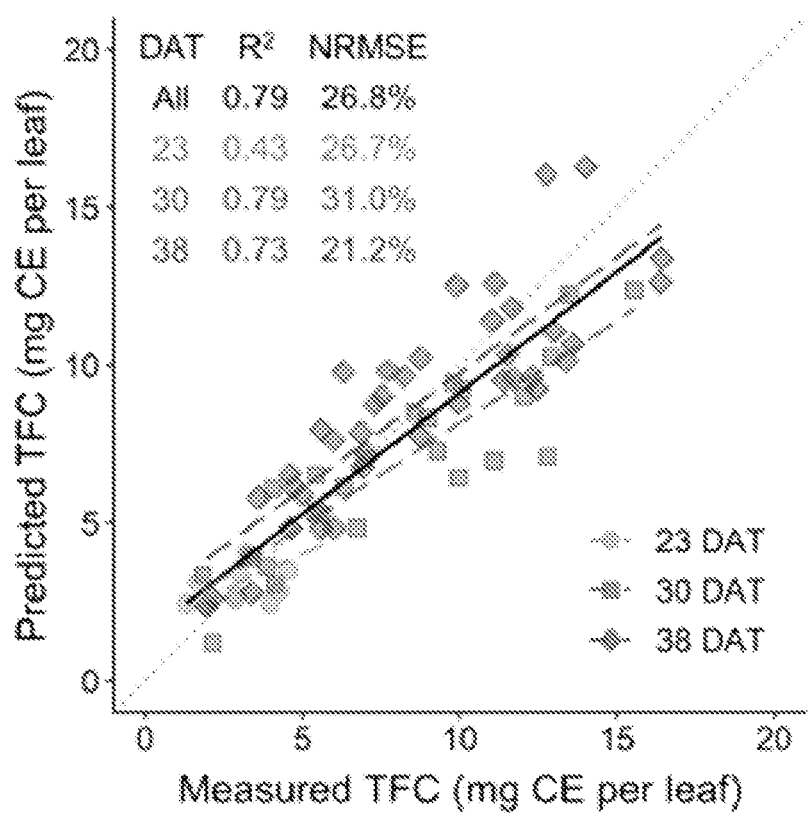

FIGS. 14A and 14B are graphs illustrating accuracy evaluation of the secondary metabolite content prediction model.

As illustrated in FIGS. 14A and 14B, a value of R2 is 0.78 to 0.79, which is verified with high accuracy. In addition, an NRMSE value, which is a relative error value, is measured as a value less than 30%, and thus, it can be seen that the secondary metabolite content prediction model has an accuracy of 70% or more.

Figure 15A:
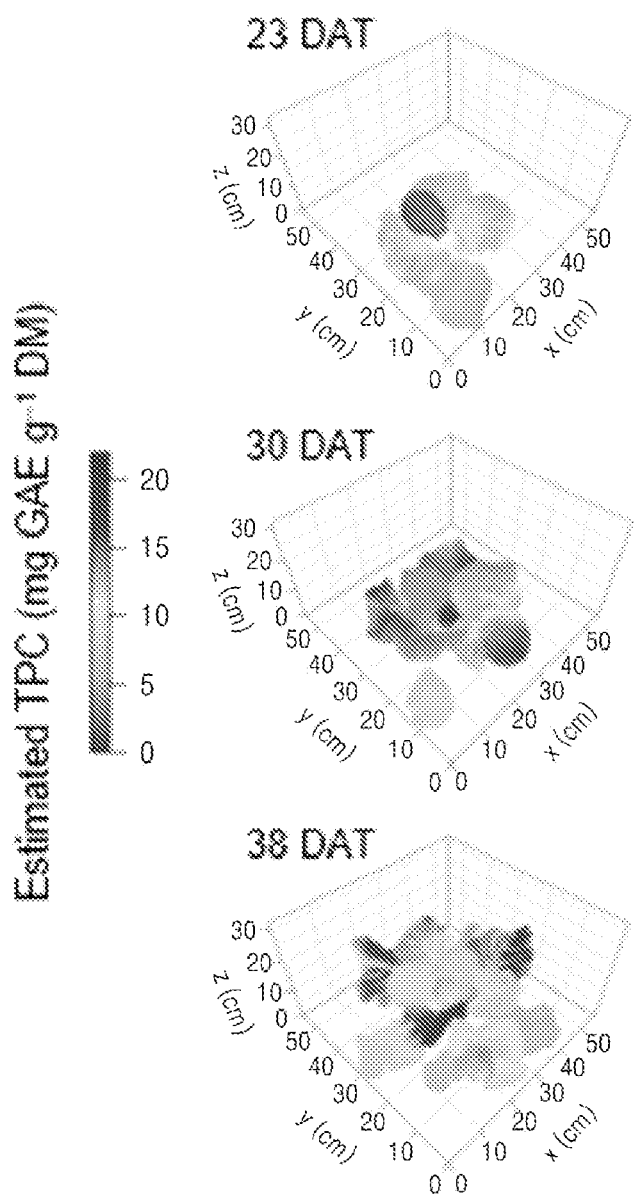
FIGS. 15A and 15B are respectively diagrams and graphs illustrating an estimated distribution of total phenolic compound content using a prediction model, according to an embodiment of the present disclosure.
Figure 15B:
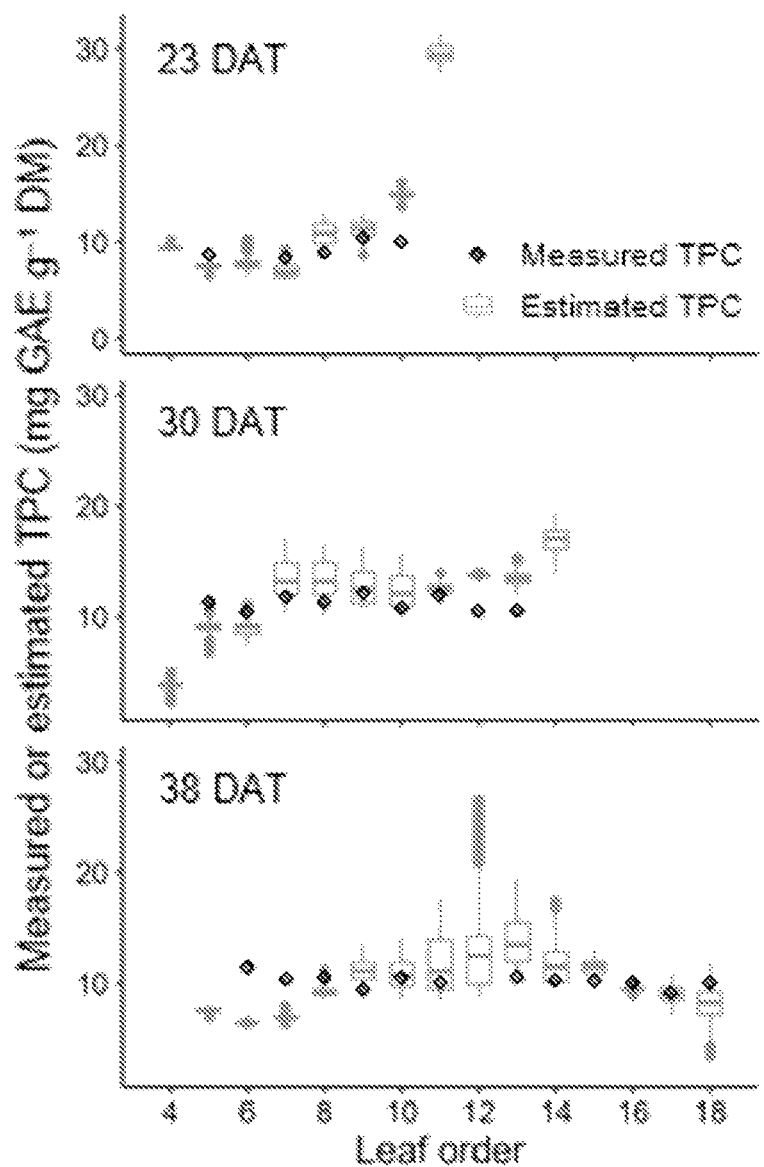

FIGS. 15A and 15B are respectively diagrams and graphs illustrating an estimated distribution of total phenolic compound content derived by using a prediction model.

FIG. 15A illustrates an estimated distribution of total phenolic compound content (TPC) of plant model according to a growth stage, and FIG. 15B illustrates graphs showing comparison results of an estimated value and an actually measured value of the total phenolic compound content depending on growth stages and an order of leaves. In FIG. 15B, box plots represent the estimated values of the total phenolic compound content, and points represent the measured values.

The secondary metabolite content prediction model according to an embodiment of the present disclosure is a model based on an ultraviolet light interception amount of a leaf. Accordingly, the model may be represented by inversely estimating a spatial distribution of content of secondary metabolites of a three-dimensional plant model.

Figure 16A:
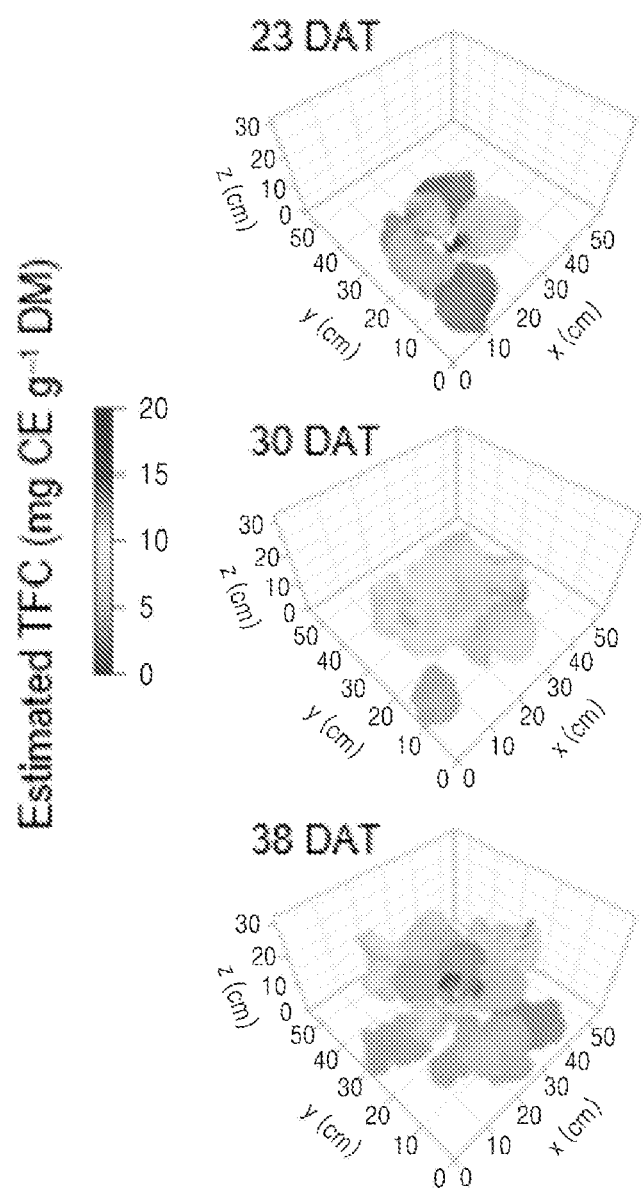
FIGS. 16A and 16B are respectively diagrams and graphs illustrating an estimated distribution of total flavonoid compound content using a prediction model, according to an embodiment of the present disclosure.
Figure 16B:
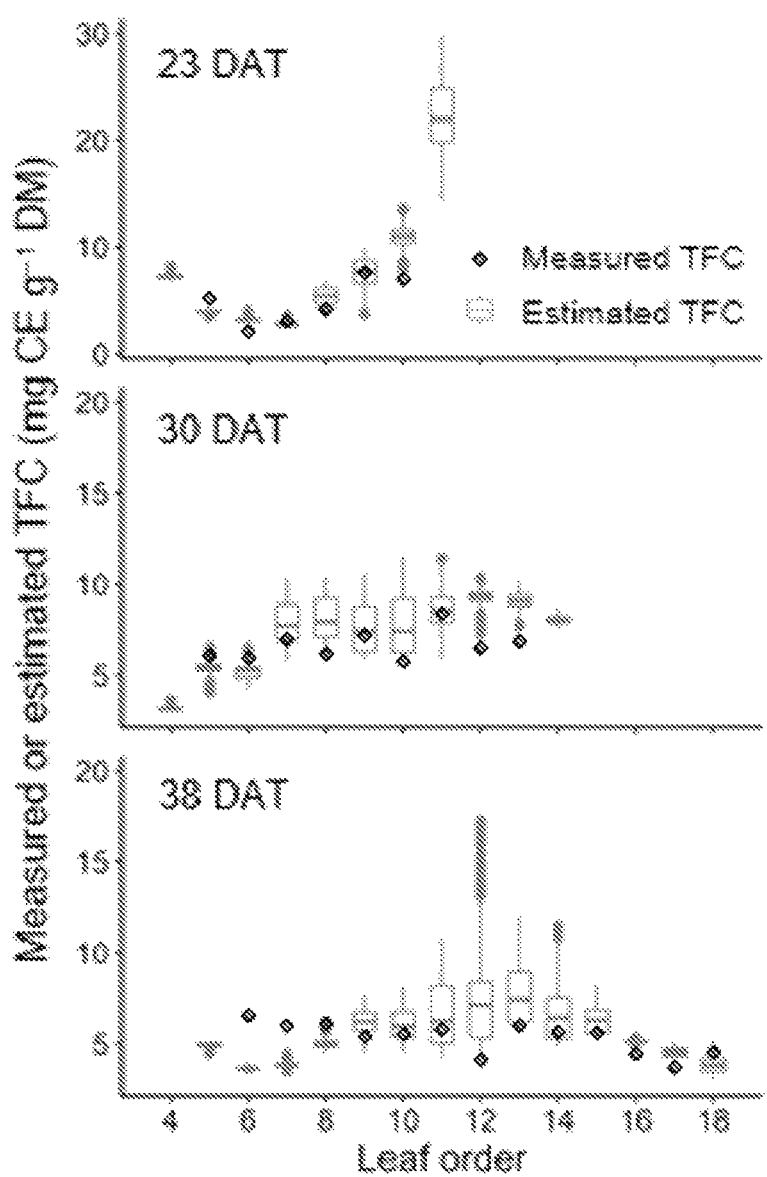

FIGS. 16A and 16B are respectively diagrams and graphs illustrating an estimated distribution of total flavonoid compound content derived by using a secondary metabolite content prediction model.

FIG. 16A illustrates an estimated distribution of total flavonoid compound content (TFC) of plant model according to growth stages of plant. FIG. 16B illustrates graphs showing comparison results of an estimated value and an actual value of the total flavonoid compound content according to growth stages and an order of leaves. In FIG. 16B, box plots represent the estimated values of the total flavonoid compound content, and points represent measured values.

Figure 17A:
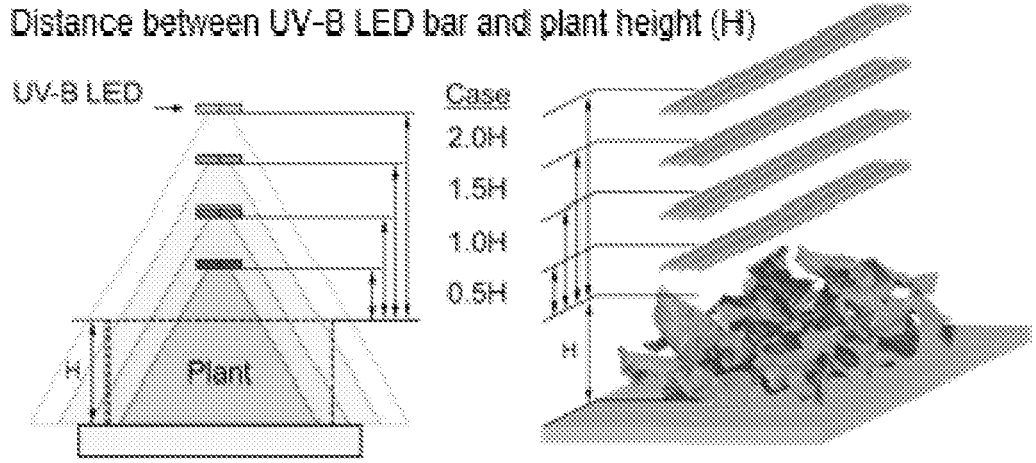
FIGS. 17A, 17B, and 17C illustrate examples of a virtual ultraviolet light source arrangement according to an embodiment of the present disclosure.
Figure 17B:
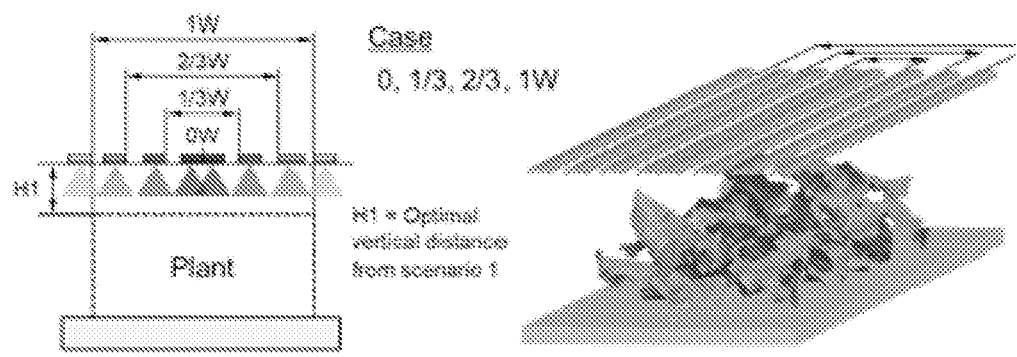
Figure 17C:
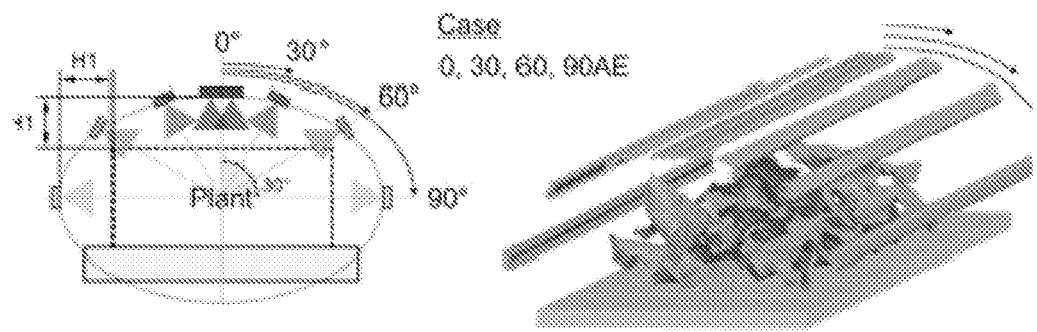

FIGS. 17A, 17B, and 17C illustrate examples of a light source arrangement of a simulation model.

FIG. 17A illustrates an example in which light sources are arranged based on a vertical distance of an ultraviolet light source from the center of an upper end portion of plant. FIG. 17B illustrates an example in which light sources are arranged based on a horizontal interval of an ultraviolet light source from the center of the upper end portion of the plant. FIG. 17C illustrates an example in which light sources are arranged according to a side irradiation angle from the center of the plant. In this case, a reference for setting a distance may be set to four levels respectively based on an average height H and an average width W of plant.

Therefore, a light source of a simulation model may be changed in a vertical distance, a horizontal interval, and a side irradiation angle with respect to the center of plant. In addition, content of secondary metabolites of plant according to the changed light source may be predicted.

Figure 18A:
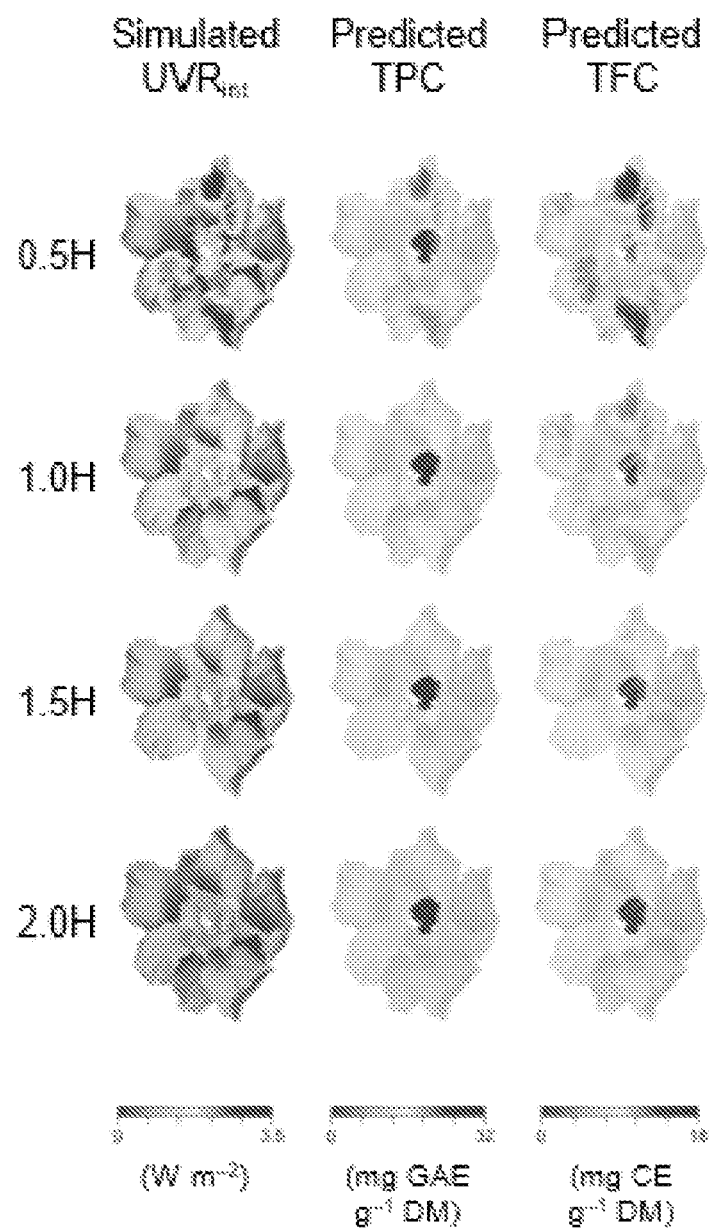
FIGS. 18A and 18B are respectively diagrams and graphs respectively illustrating ultraviolet light interception analysis and secondary metabolite estimation according to a vertical distance of an ultraviolet light source.
Figure 18B:
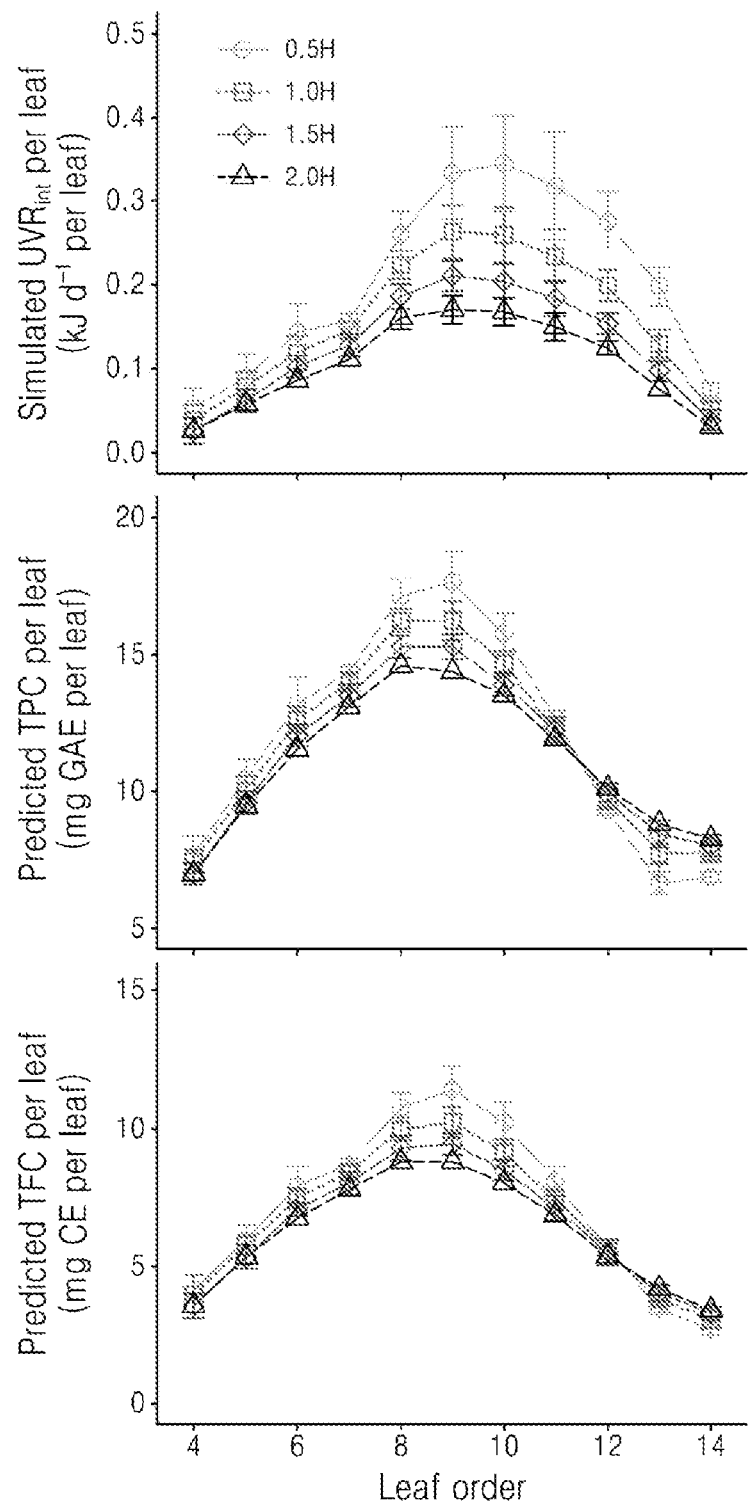

FIGS. 18A and 18B are respectively diagrams and graphs illustrating ultraviolet light interception analysis and estimation of secondary metabolites according to a vertical distance of an ultraviolet light source.

FIG. 18A illustrates an ultraviolet light interception amount of plant model and an estimated distribution of phenol and flavonoid compound content according to growth stages. FIG. 18B illustrates the ultraviolet light interception amount and the estimated distribution of the phenol and flavonoid compound content according to the growth stages and an order of leaves.

As illustrated in FIGS. 18A and 18B, as a vertical irradiation distance of a light source is closer, a predicted value of a light interception amount of plant model increases. In addition, as the vertical irradiation distance of the light source is closer, a predicted value of total phenolic compound content and total flavonoid compound content of the plant model also increase.

In FIGS. 18A and 18B, vertical distances with the highest predicted values of the total light interception amount and content of secondary metabolites of plant model are derived as 0.5H. Accordingly, 0.5H may be determined as an optimal value of a vertical irradiation distance, and conditions of the simulation model and an actual plant cultivation environment may be changed by using the optimal value.

That is, the simulation model derives predicted values of an ultraviolet light interception amount and content of secondary metabolites of plant according to a vertical distance of a light source, and the simulation model or setting of the light source in an actual plant cultivation environment may be changed by using the derived results.

Figure 19A:
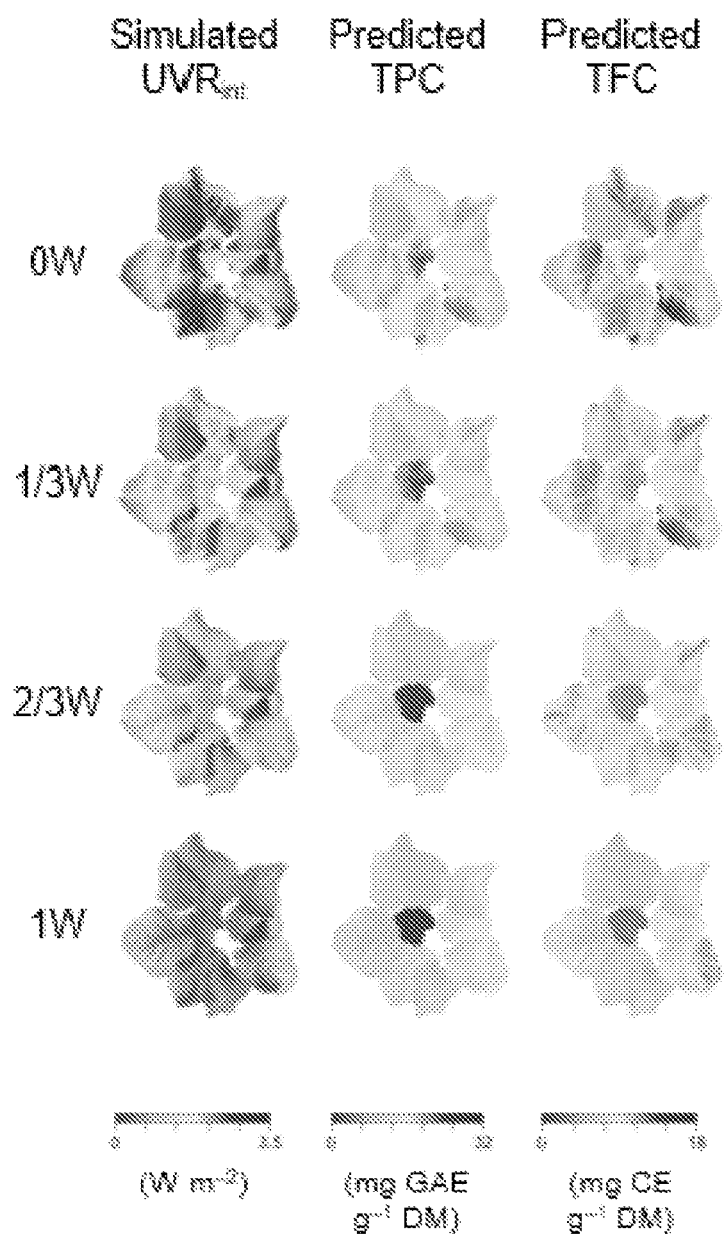
FIGS. 19A and 19B are respectively diagrams and graphs illustrating ultraviolet light interception analysis and secondary metabolite estimation according to a horizontal interval of an ultraviolet light source.
Figure 19B:
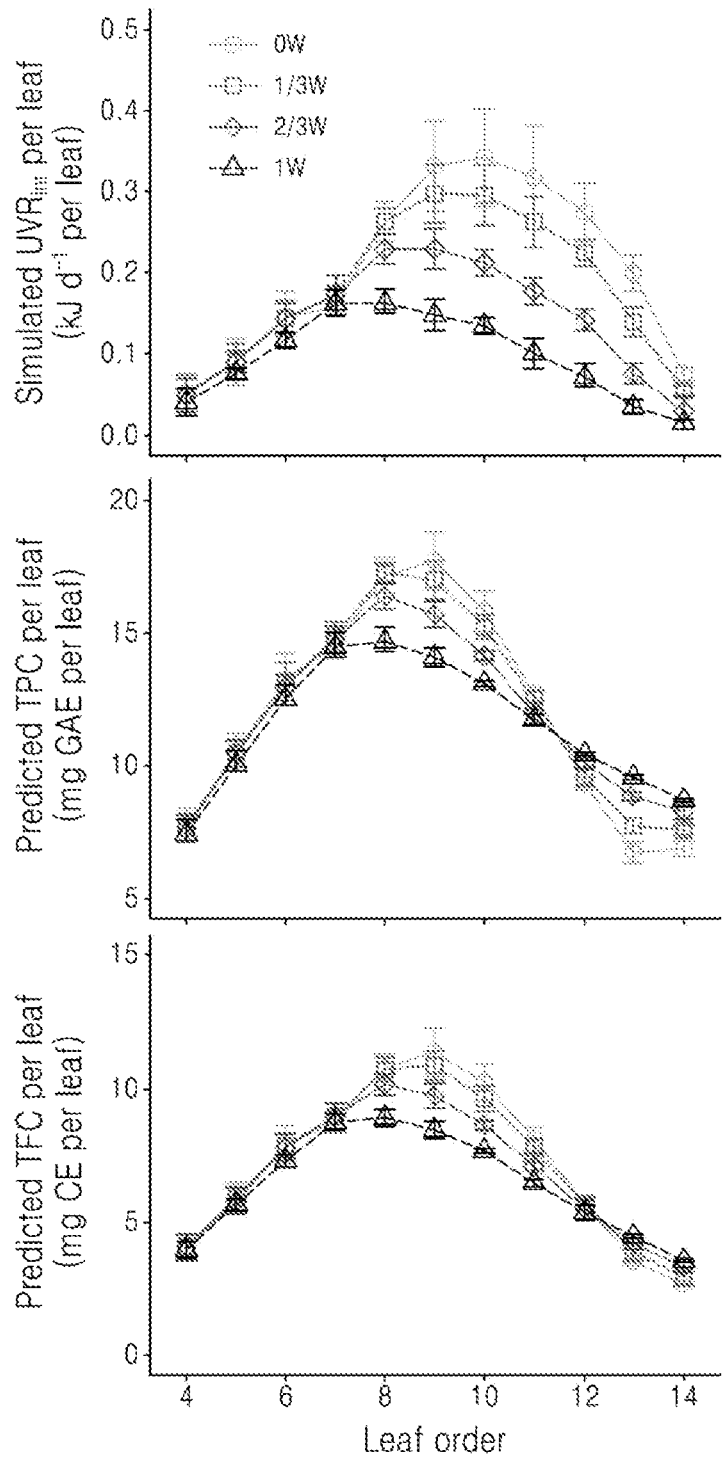

FIGS. 19A and 19B are respectively diagrams and graphs illustrating ultraviolet light interception analysis and estimation of secondary metabolites according to a horizontal interval of an ultraviolet light source.

FIG. 19A illustrates estimated distributions of an ultraviolet light interception amount and content of phenol and flavonoid compounds of plant model according to growth stages. FIG. 19B illustrates estimated distributions of an ultraviolet light interception amount and content of phenol and flavonoid compounds according to growth stages and an order of leaves.

As illustrated in FIGS. 19A and 19B, as a horizontal interval (an interval between a pair of LED modules) of a light source is further away from the center of plant, a predicted value of the light interception amount of a leaf at the middle and lower portion corresponding to a leaf at both ends of the plant increases. In addition, as the predicted value of the light interception amount increases, predicted values of total phenolic compound content and total flavonoid compound content also increase.

As illustrated in FIGS. 19A and 19B, a horizontal interval of a light source having the highest predicted values of a total light interception amount and content of secondary metabolites of plant model is derived, and conditions of a simulation model and an actual plant cultivation environment may be changed by using the derived horizontal interval.

That is, a simulation model may derive predicted values of an ultraviolet light interception amount and content of secondary metabolites of plant according to a horizontal interval of a light source and change setting of a light source of a simulation model or an actual plant cultivation environment by using the derived results.

Figure 20A:
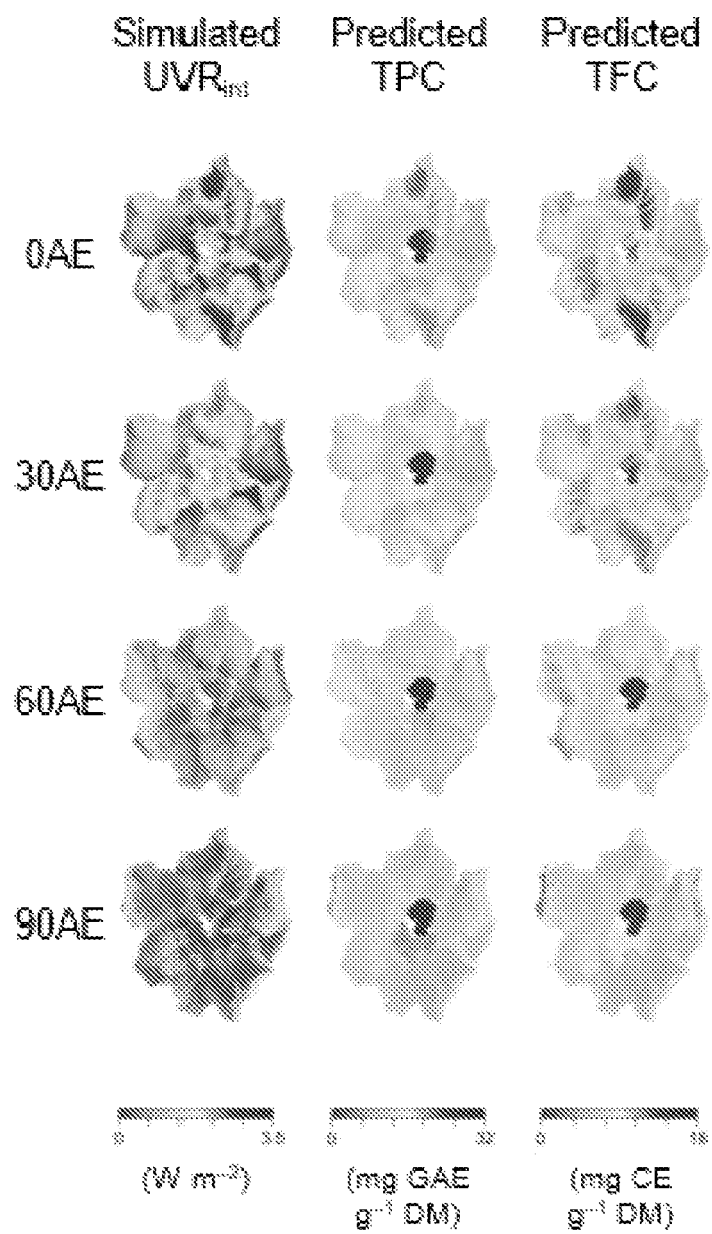
FIGS. 20A and 20B are respectively diagrams and graphs illustrating ultraviolet light interception analysis and secondary metabolite estimation according to a side irradiation angle of an ultraviolet light source.
Figure 20B:
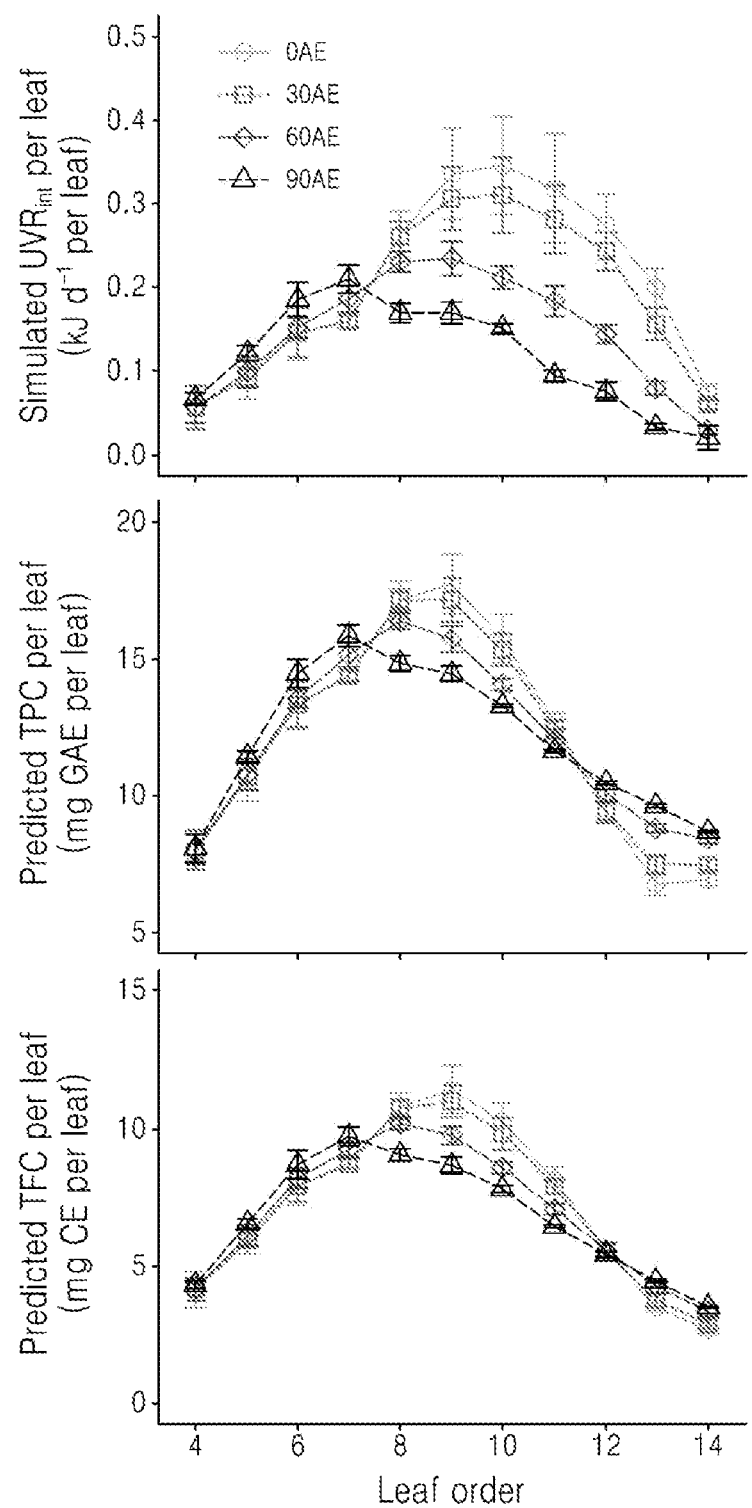

FIGS. 20A and 20B are diagrams and graphs illustrating ultraviolet light interception analysis and estimation of secondary metabolites according to a side irradiation angle of an ultraviolet light source.

FIG. 20A illustrates estimated distributions of an ultraviolet light interception amount and content of phenol and flavonoid compounds of plant model according to growth stages. FIG. 20B illustrates estimated distributions of an ultraviolet light interception amount and content of phenol and flavonoid compounds according to growth stages and an order of leaves.

As illustrated in FIGS. 20A and 20B, when side irradiation angles are 60 degrees and 90 degrees during light irradiation, predicted values of a light interception amount and content of secondary metabolites of a middle and lower leaf are significantly increased.

That is, a simulation model may derive predicted values of an ultraviolet light interception amount and content of secondary metabolites of plant according to a side irradiation angle of a light source and change setting of a light source in a simulation model or an actual plant cultivation environment by using the derived results.

Figure 21:
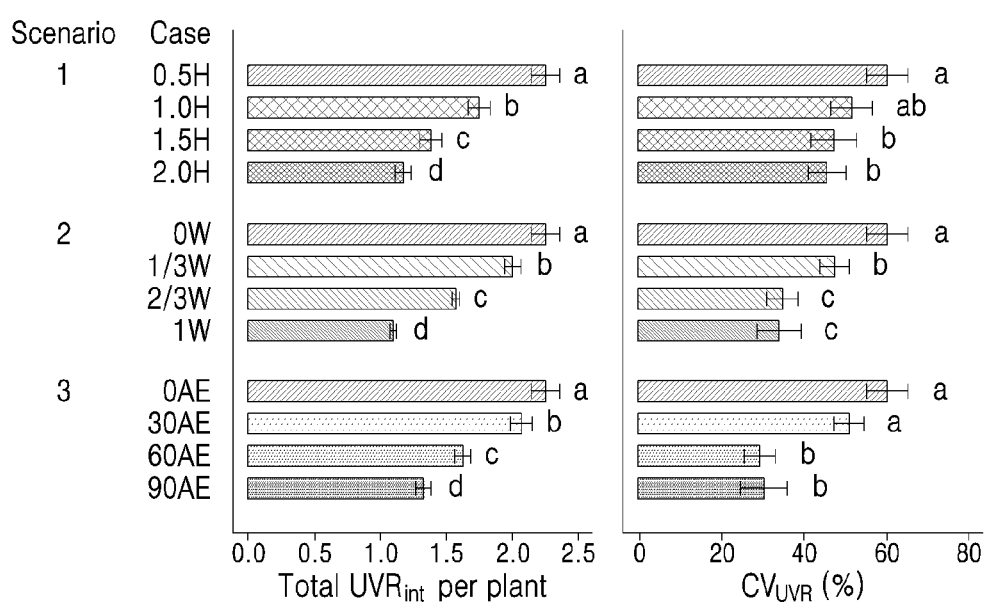
FIG. 21 is a graph illustrating an ultraviolet light interception amount and uniformity evaluation according to ultraviolet light source arrangement of a simulation model.

FIG. 21 is a graph illustrating evaluation of an ultraviolet light interception and uniformity according to a light source arrangement of a simulation model.

According to an evaluation method of an artificial light source setting method for controlling secondary metabolites of plant, an ultraviolet light interception amount, content of secondary metabolites, and energy use efficiency (RUE) and uniformity (low CV) for the content of secondary metabolites may be evaluated.

FIG. 21 illustrates a total ultraviolet light interception amount according to a vertical distance H, a horizontal interval W, and a side irradiation angle AE of a light source of a simulation model and coefficients of variance of the light interception amount. Total UVRint per plant represents a total ultraviolet light interception amount of plant, and CVUVR represents a coefficient of variance of an ultraviolet light interception amount between leaves. Accordingly, the smaller the coefficient of variance (CV), the more uniform the ultraviolet light interception amount between the leaves.

Figure 22:
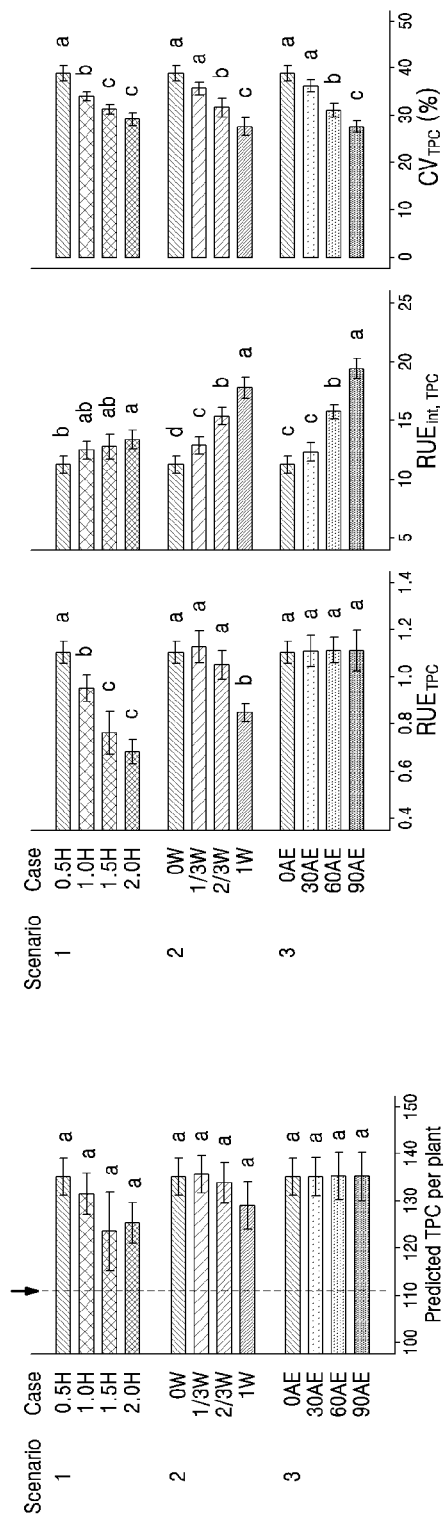
FIG. 22 is a graph illustrating evaluation of phenolic compound content according to ultraviolet light source arrangement of a simulation model.

FIG. 22 illustrates graphs showing evaluation of phenolic compound content according to an arrangement of light sources of a simulation model.

As illustrated in FIG. 22, total phenolic compound content (TPC) and energy use efficiency (RUE) per plant object are highest when a vertical distance of a light source is 0.5H, a horizontal interval therebetween is ⅓ W, and a side irradiation angle thereof is 60AE. In addition, when a horizontal arrangement of a light source is greater than a certain distance from the center, both efficiency and uniformity of the total phenolic compound content appear are increased.

Figure 23:
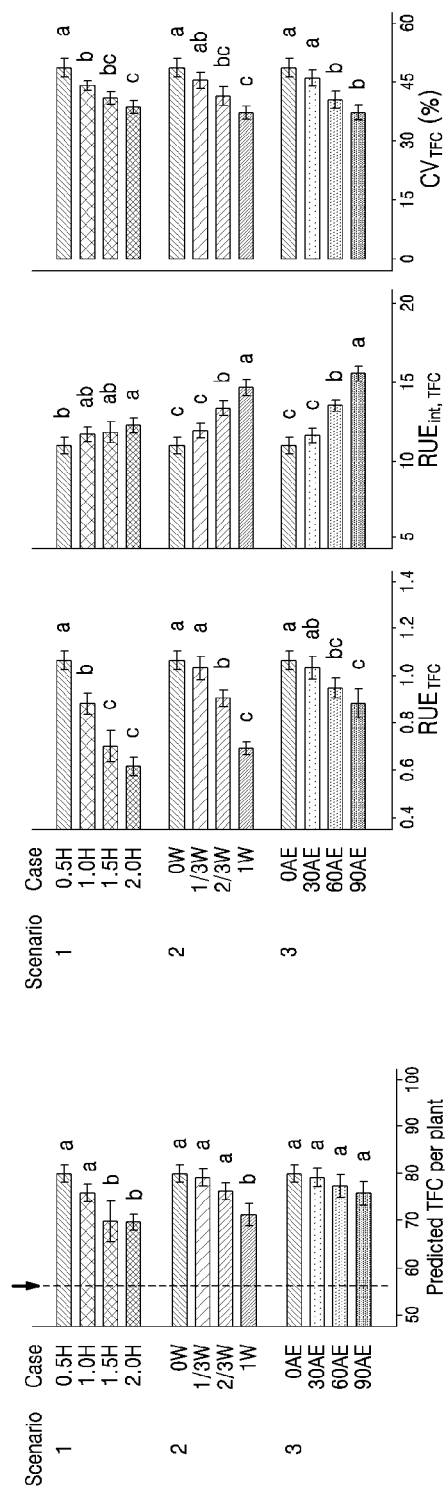
FIG. 23 is a graph illustrating evaluation of flavonoid compound content according to ultraviolet light source arrangement of a simulation model.

FIG. 23 illustrates graphs showing evaluation of flavonoid compound content according to an arrangement of light sources of a simulation model.

As illustrated in FIG. 23, the total flavonoid compound content (TFC) per plant object and energy use efficiency (RUE) are highest when a vertical distance of a light source is 0.5H. In addition, when a horizontal arrangement of a light source is more than a certain distance from the center, uniformity of the total flavonoid compound content is increased, but efficiency is decreased.

Therefore, in order to control total phenolic compound content of plant, all of a vertical distance, a horizontal interval, and a side irradiation angle between plant and a light source have to be considered. However, flavonoid content is less affected by the horizontal interval and the side irradiation angle of the light source compared to the vertical distance of the light source, and thus, only the vertical distance of the light source may be considered to control total flavonoid content of plant.

As described above, a difference in ultraviolet light interception of a leaf depending on growth stages of plant may be quantitatively predicted by using an optical simulation program. In addition, as a result of analysis, bioactive compound and antioxidant activity change depending on cumulative UV light interception values by an UV LED and positions of a leaf in different growth stages. In addition, increase efficiency of secondary metabolites may be compared with absorbed UV energy.

In addition, it is possible to predict content of secondary metabolites for each growth stage and each leaf using an ultraviolet light interception value by using the simulation model, to estimate content of secondary metabolites according to a virtual ultraviolet light source arrangement by using a prediction model, and to evaluate a light source arrangement. That is, a vertical distance, a horizontal interval, and a side irradiation angle of a light source may be set by using a simulation model, and an ultraviolet light interception value, content of secondary metabolites, energy use efficiency, and a coefficient of variation of plant may be derived according thereto. In addition, setting of a light source in an actual plant cultivation environment may be changed by using an ultraviolet light interception value, content of secondary metabolites, energy use efficiency, and a coefficient of variation of plant according to a vertical distance, a horizontal interval, and a side irradiation angle of a light source derived by using a simulation model.

Therefore, an ultraviolet light interception distribution of plant according to light source data and content of secondary metabolites according thereto may be analyzed by using a simulation model, and a light source setting value for deriving content of a target secondary metabolite may be derived.

An embodiment of the present disclosure may be implemented in the form of a recording medium including instructions executable by a computer, such as a program module executed by the computer. A computer-readable recording medium may be any available medium that may be accessed by a computer and include both volatile and non-volatile media and removable and non-removable media. In addition, the computer-readable recording medium may include both a computer storage medium and a communication medium. The computer storage medium includes both volatile and non-volatile media and removable and non-removable media implemented by any method or technology for storing information such as computer readable instructions, data structures, program modules, or other data.

Although the method and system according to the present disclosure are described with reference to some embodiments, some or all of components or operations thereof may be implemented by using a computer system having a general purpose hardware architecture.

The above descriptions on the present disclosure are examples, and those skilled in the art to which the present disclosure belongs may understand that the examples may be easily modified into other specific forms without changing the technical idea or essential features of the present disclosure. Therefore, it should be understood that the embodiments described above are illustrative in all respects and not restrictive. For example, each component described as a single type may be implemented in a distributed form, and likewise components described in the distributed form may be implemented in a combined form.

The scope of the present disclosure is indicated by the following claims rather than the detailed description made above, and all changes or modifications derived from the meaning and scope of the claims and their equivalent concepts should be interpreted as being included in the scope of the present disclosure.

What is claimed is:

1. An artificial light source setting method for controlling secondary metabolites of plant, the artificial light source setting method comprising:
generating a simulation model by using a three-dimensional structure model of the plant and light source data of a plant factory;
predicting content of secondary metabolites of each of a plurality of leaves by analyzing light interception of each of the plurality of leaves included in the three-dimensional structure model of the plant; and
deriving a light source setting value such that the content of secondary metabolites of each of the plurality of leaves has a preset value and changing an artificial light source setting of the plant factory according to the light source setting value,
wherein the generating of the simulation model comprises: generating three-dimensional scan data of the plant by using a three-dimensional scanner; and generating a surface model by using the three-dimensional scan data,
wherein the predicting of the content of secondary metabolites comprises: setting each of the plurality of leaves included in the surface model as a detector; and predicting a light interception amount of each of the plurality of leaves of the plant, and
wherein the predicting of the content of secondary metabolites further comprises: receiving data on optical properties and the content of secondary metabolite of the plant; and performing linear regression analysis on the optical properties and the content of secondary metabolites of the plant.

2. The artificial light source setting method of claim 1, wherein the predicting the content of secondary metabolites further comprises:
deriving the light interception amount according to any one of each leaf of the plant and a growth stage of the plant by using a prediction result of the light interception amount for each leaf; and
predicting the content of secondary metabolites by using the light interception amount according to any one of each leaf of the plant and the growth stage of the plant and a result of the linear regression analysis.

3. The artificial light source setting method of claim 1, wherein
the predicting of the content of secondary metabolites comprises predicting an ultraviolet light interception value and the content of secondary metabolites according to a vertical distance between a light source included in the simulation model and the three-dimensional structure model of the plant, a horizontal interval of the light source, and a side irradiation angle of the light source, and
the changing of the artificial light source setting of the plant factory is performed based on the ultraviolet light interception value and the content of secondary metabolites according to the vertical distance, the horizontal interval, and the side irradiation angle.

4. An artificial light source setting system for controlling secondary metabolites of plant, the artificial light source setting system comprising:
an artificial ultraviolet light source configured to generate light for cultivation of plant;
a memory in which an optical simulation program is stored;
a processor configured to execute an optical simulation program stored in the memory; and
a three-dimensional scanner configured to scan the plant to generate three-dimensional scan data of the plant,
wherein the processor executes the optical simulation program to generate a simulation model by using a three-dimensional structure model of the plant and light source data of a plant factory, predicting content of secondary metabolites of each of a plurality of leaves by analyzing light interception of each of the plurality of leaves included in the three-dimensional structure model of the plant, and deriving a light source setting value such that the content of secondary metabolites of each of the plurality of leaves has a preset value,
wherein the artificial light source is controlled according to the light source setting value,
wherein the processor executes the optical simulation program to generate a surface model by using the three-dimensional scan data,
wherein the processor executes the optical simulation program to set each of the plurality of leaves included in the three-dimensional structure model of the plant as a detector, predict the light interception amount of each leaf of the plant, and predict the content of secondary metabolites accordingly, and
wherein the processor executes the optical simulation program to receive data on optical properties and the content of secondary metabolite of the plant and perform linear regression analysis on the optical properties and the content of secondary metabolites of the plant.

5. The artificial light source setting system of claim 4, wherein the processor executes the optical simulation program to derive the light interception amount according to any one of each leaf of the plant and a growth stage of the plant by using a prediction result of the light interception amount for each leaf; and predict the content of secondary metabolites by using the light interception amount according to any one of each leaf of the plant and the growth stage of the plant and a result of the linear regression analysis.

6. The artificial light source setting system of claim 4, wherein the processor executes the optical simulation program to predicting an ultraviolet light interception value and the content of secondary metabolites according to a vertical distance between a light source included in the simulation model and the three-dimensional structure model of the plant, a horizontal interval of the light source, and a side irradiation angle of the light source, and setting of the artificial light source of the plant factory is changed based on the ultraviolet light interception value and the content of secondary metabolites according to the vertical distance, the horizontal interval, and the side irradiation angle.

\* \* \* \* \*